(12) United States Patent
Hackam

(10) Patent No.: US 8,518,903 B2
(45) Date of Patent: *Aug. 27, 2013

(54) USE OF TOLL-LIKE RECEPTOR-9 AGONISTS

(75) Inventor: David J. Hackam, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/068,553

(22) Filed: May 13, 2011

(65) Prior Publication Data

US 2012/0077868 A1    Mar. 29, 2012

Related U.S. Application Data

(63) Continuation-in-part of application No. 12/104,816, filed on Apr. 17, 2008, now Pat. No. 8,188,058.

(60) Provisional application No. 61/027,728, filed on Feb. 11, 2008, provisional application No. 60/912,862, filed on Apr. 19, 2007, provisional application No. 61/334,999, filed on May 14, 2010.

(51) Int. Cl.
  *A61K 31/7084* (2006.01)
  *A61K 38/05* (2006.01)
  *A61K 38/12* (2006.01)
  *A61K 39/395* (2006.01)

(52) U.S. Cl.
  USPC .................... 514/44 R; 514/12.2; 514/2.4

(58) Field of Classification Search
  None
  See application file for complete search history.

(56) References Cited

U.S. PATENT DOCUMENTS

| | | | |
|---|---|---|---|
| 4,357,322 A | 11/1982 | Rooks et al. | |
| 5,506,204 A | 4/1996 | Aston | |
| 6,214,806 B1 | 4/2001 | Krieg et al. | |
| 6,613,751 B2 | 9/2003 | Raz et al. | |
| 7,038,029 B2 | 5/2006 | Lopez | |
| 7,049,302 B1 | 5/2006 | Kensil | |
| 7,129,222 B2 | 10/2006 | Van Nest et al. | |
| 7,183,111 B2 | 2/2007 | Van Nest et al. | |
| 8,188,058 B2 | 5/2012 | Hackam | |
| 2006/0211752 A1 | 9/2006 | Kohn et al. | |
| 2007/0004654 A1 | 1/2007 | Raz et al. | |

FOREIGN PATENT DOCUMENTS

| WO | WO2004/096156 | 11/2004 |
|---|---|---|
| WO | WO2007/120368 | 10/2007 |

OTHER PUBLICATIONS

Michaelsson et al., J. Immunol. 176(10):5741-8.
Merck Manual website, Nov. 2007 by William J. Cochran, MD. Downloaded on Nov. 7, 2011 from www.merckmanuals.com/professional/pediatrics/gastrointestinal_disorders_in_neonates_and_infants/necrotizing_enterocolitis.
Panigrahi, 2006, Paediatr. Drugs 8(3):151-165.
Thompson and Bizzaro, 2008, Drugs 68(9):1227-1238.
Achkar, 2007, Cleveland Clinic J. Med. 74(9):657-660.
U.S. Appl. No. 13/461,672, filed May 1, 2012.
U.S. Appl. No. 12/104,816, filed Apr. 17, 2008.
U.S. Appl. No. 12/104,816, May 10, 2011 Final Office Action.
U.S. Appl. No. 12/104,816, Feb. 24, 2011 Response to Non-Final Office Action.
U.S. Appl. No. 12/104,816, Nov. 24, 2010 Non-Final Office Action.
Sodhi, et al., "Toll-like receptor-4 inhibits enterocyte proliferation via impaired b-catenin signaling in necrotizing enterocolitis", Gastroenterology 2010, 138(1): 185-196.
Van Heel et al., "Synergy between TLR9 and NOD2 innate immune responses is lost in genetic Crohn's disease" GUT, British Medical Association, Nov. 1, 2005, 54(11):1553-1557.
Fukata et al., "TLR4 signalling in the intestine in health and disease" Biochemical Society Transactions, Dec. 1, 2007, 35(6):1473-1478.
Caplan et al., "Neonatal necrotizing enterocolitis: possible role of probiotic supplementation", Journal of Pediatric Gastroenterology and Nutrition, Mar. 1, 2000, 30(2): S18-S22.
Tatum et al. "The role of toll-like receptor 9 in an animal model of necrotizing enterocolotis" Journal of Investigative Medicine, Feb. 1, 2010, 58(2): 436.
Gribar et al., "Reciprocal expression and signalling of TLR4 and TLR9 in the pathogenesis and treatment of necrotizing enterocolitis" Journal of Immunologists, Jan. 1, 2009, 182(1): 636-646.
Supplemental European Search Report for EP Application No. 08746070.5 dated May 25, 2011.
Shan et al., 2006, "Regulation of Toll-like receptor 4-induced proasthmatic changes in airway smooth muscle function by opposing actions of ERK1/2 and p38 MAPK signaling." Am J Physiol Lung Cell Mol Physiol. 291(3):L324-33. Epub Mar. 31, 2006.
University of Pittsburgh Department of Cirtical Care Medicine: Research—The Crisma Laboratory. pp. 1-11. Downloaded on Apr. 19, 2007 from http://www.ccm.upmc.edu/research/res_crisma.html.
Career Opportunities—Eisai announces PhaseII results, plans to iniate phase III clinical—Aug. 29, 2005. Downloaded on Apr. 18, 2007 from http://www.eisai.com/view_pressJelease.asp?ID=145&press=124.
Zhai et al., 2004, "Cutting edge: TLR4 activation mediates liver ischemia/reperfusion inflammatory response via IFN regulatory factor 3-dependent MyD88-independent pathway." J Immunol. 173(12):7115-9.
Shuto et al., 2001, "Activation of NF-kappa B by nontypeable Hemophilus influenzae is mediated by toll-like receptor 2-TAK1-dependent NIK-IKK alpha /beta-I kappa B alpha and MKK3/6-p38 MAP kinase signaling pathways in epithelial cells." Proc Natl Acad Sci U S A. 98(15):8774-9. Epub Jul. 3, 2001.
Obermeier, et al., 2003, "Contrasting activity of cytosin-guanosin dinucleotide oligonucleotides in mice with experimental colitis." Clin Exp Immunol. 134(2):217-24.
Jilling et al., 2006, "The roles of bacteria and TLR4 in rat and murine models of necrotizing enterocolitis." J Immunol. 177(5):3273-82.
Prohinar et al., 2007, "Specific high affinity interactions of monomeric endotoxin.protein complexes with Toll-like receptor 4 ectodomain." J Biol Chem. 282(2):1010-7. Epub Nov. 22, 2006.
Neal et al., 2006, "Enterocyte TLR4 mediates phagocytosis and translocation of bacteria across the intestinal barrier." J Immunol. 176(5):3070-9.
Kobayashi et al., 1998, "Suppression of murine endotokin response by E5531, a novel synthetic lipid A antagonist." Antimicrob Agents Chemother. 42(11):2824-9.

(Continued)

*Primary Examiner* — Sean McGarry
(74) *Attorney, Agent, or Firm* — Baker Botts, L.L.P.

(57) ABSTRACT

The present invention relates to the use of a TLR9 agonist and/or a TLR4 antagonist and/or a NOD2 agonist for treatment or prevention of disorders involving TLR4 activation, such as systemic sepsis and necrotizing enterocolitis.

4 Claims, 33 Drawing Sheets

Figure 15:
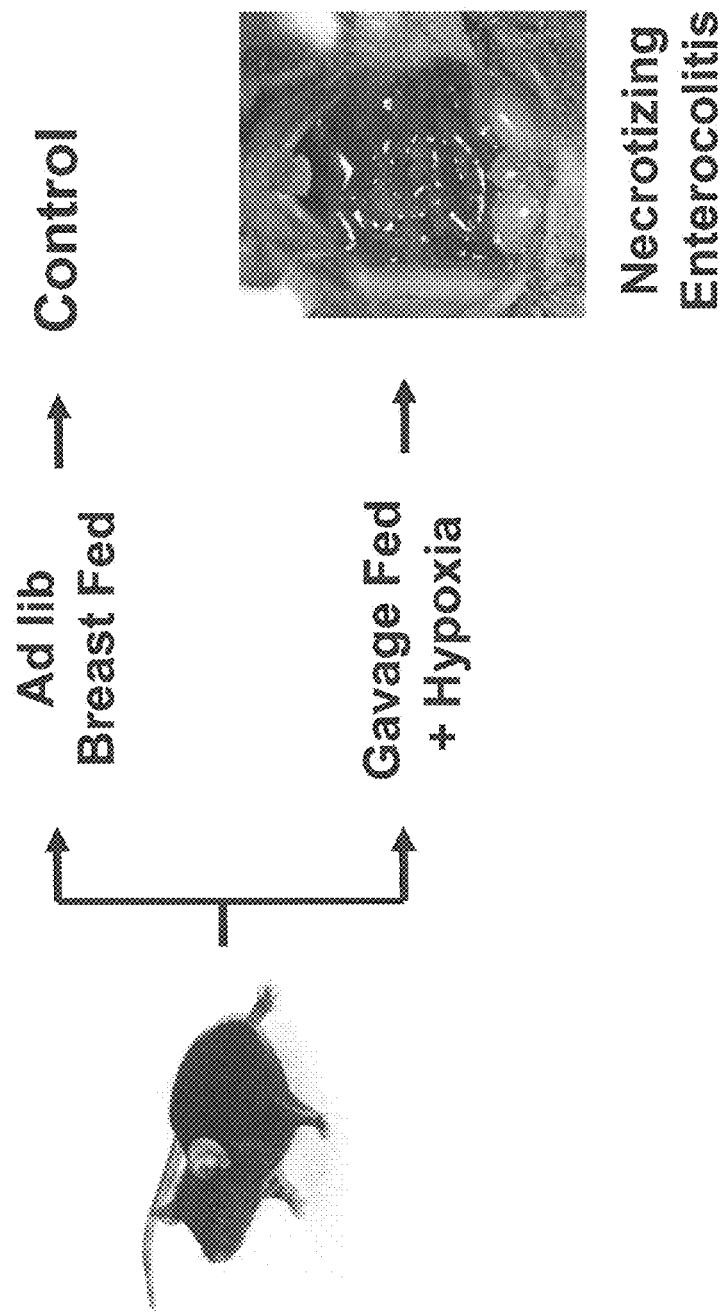

(6 of 33 Drawing Sheet(s) Filed in Color)

(56) References Cited

OTHER PUBLICATIONS

Hugot et al., 2001, "Association of NOD2 leucine-rich repeat variants with susceptibility to Crohn's disease." Nature. 411(6837):599-603.
Ogura et al., 2001, "A frameshift mutation in NOD2 associated with susceptibility to Crohn's disease." Nature. 411(6837):603-6.
Watanabe et al., 2008, "Muramyl dipeptide activation of nucleotide-binding oligomerization domain 2 protects mice from experimental colitis." J Clin Invest 118:545-559.
Yang et al., 2007, "NOD2 transgenic mice exhibit enhanced MDP-mediated down-regulation of TLR2 responses and resistance to colitis induction." Gastroenterology 133:1510-1521.
Verthelyi et al., 2001, "Human peripheral blood cells differentially recognize and respond to two distinct CPG motifs." J Immunol. 166(4):2372-7.
Wirtz et al. 2005, "Illuminating the role of type I IFNs in colitis." J Clin Invest. 115(3):586-8.
Katakura et al., 2005, "Toll-like receptor 9-induced type I IFN protects mice from experimental colitis." J Clin Invest. 115(3):695-702. Erratum in: J Clin Invest. 2005, 115(4):1100.
Ewaschuk et al., 2007, "Surface expression of Toll-like receptor 9 is upregulated on intestinal epithelial cells in response to pathogenic bacterial DNA." Infect Immun. 75(5):2572-9. Epub Feb. 26, 2007.
Putta et al., 2006, "Novel oligodeoxynucleotide agonists of TLR9 containing N3-Me-dC or N1-Me-dG modifications." Nucleic Acids Res. 34(11):3231-8.
Rossignol et al., 2004, "Safety, pharmacokinetics, pharmacodynamics, and plasma lipoprotein distribution of eritoran (E5564) during continuous intravenous infusion into healthy volunteers." Antimicrob Agents Chemother. 48(9):3233-40.
Mullarkey et al., 2003, "Inhibition of endotoxin response by e5564, a novel Toll-like receptor 4-directed endotoxin antagonist." J Pharmacol Exp Ther. 304(3):1093-102.
Anand et al., 2007, "The Role of the Intestinal Barrier in the Pathogenesis of Necrotizing Enterocolitis." Shock 27:124-133.
Neu, 1996, "Necrotizing enterocolitis: the search for a unifying pathogenic theory leading to prevention." Pediatr Clin North Am. 43(2):409-32.
Carneiro et al., 2008, "Nod-like proteins in inflammation and disease." J Pathol. 214(2):136-48.
Franchi et al., 2008, "Intracellular NOD-like receptors in innate immunity, infection and disease." Cell Microbiol 10:1-8.
Aki Tsukioka, "Eisai Successfully Completes Phase II Trial of Eritoran, Drug Candidate for Severe Sepsis." JCN Network, Aug. 30, 2005 p. 1. Downloaded on Nov. 20, 2009 from http://www.japancorp.net/printarticle.asp?Art_ID=10765.
Ding et al., 1998, "Characterization and quantitation of NF-kappaB nuclear translocation induced by interleukin-1 and tumor necrosis factor-alpha. Development and use of a high capacity fluorescence cytometric system." J Biol Chem. 273(44):28897-905.
Leaphart et al., 2007, "Interferon-gamma inhibits intestinal restitution by preventing gap junction communication between enterocytes." Gastroenterology. 132(7):2395-411. Epub Mar. 21, 2007.
Cetin et al., 2007, "Nitric oxide inhibits enterocyte migration through activation of RhoA-GTPase in a SHP-2-dependent manner." Am J Physiol Gastrointest Liver Physiol 292:G1347-1358.
Yang et al., 2007, "NOD2 pathway activation by MDP or Mycobacterium tuberculosis infection involves the stable polyubiquitination of Rip2." J Biol Chem 282:36223-36229.
Halpern et al., 2006, "Reduction of experimental necrotizing enterocolitis with anti-TNF-α." Am J. Physiol Gastrointest Liver Physiol 290, pp. G757-G764.
Feng et al., 2005, "Heparin-binding EGF-like growth factor (HB-EGF) and necrotizing enterocolitis." Semin Pediatr Surg. 14(3):167-74.
Henry et al., 2005, "Surgical therapy for necrotizing enterocolitis: bringing evidence to the bedside." Semin Pediatr Surg. 14(3):181-90.
Warner et al., 2005, "Role of epidermal growth factor in the pathogenesis of neonatal necrotizing enterocolitis." Semin Pediatr Surg. 14(3):175-80.

Hsueh et al., 2003, "Neonatal necrotizing enterocolitis: clinical considerations and pathogenetic concepts." Pediatr Dev Pathol 6:6-23.
Shin et al., 2000, "Diminished epidermal growth factor levels in infants with necrotizing enterocolitis." J Pediatr Surg. 35(2):173-6; discussion 177.
Ng, 2001, "Necrotizing enterocolitis in the full-term neonate." J Paediatr Child Health. 37(1):1-4.
Cetin et al., 2004, "Endotoxin inhibits intestinal epithelial restitution through activation of Rho-GTPase and increased focal adhesions." J Biol Chem. 279(23):24592-600. Epub Mar. 30, 2004.
Cario et al., 2000, "Lipopolysaccharide activates distinct signaling pathways in intestinal epithelial cell lines expressing Toll-like receptors." J Immunol. 164(2):966-72.
Otte et al., 2004, "Mechanisms of cross hyporesponsiveness to Toll-like receptor bacterial ligands in intestinal epithelial cells." Gastroenterology. 126(4):1054-70.
Kanneganti et al., 2007, "Intracellular NOD-like receptors in host defense and disease," Immunity 27:549-559.
Leaphart et al., 2007. "A Critical Role for TLR4 in the Pathogenesis of Necrotizing Enterocolitis by Modulating Intestinal Injury and Repair." J Immunology 179:4808-4820.
Sharma et al., 2007, "Neonatal gut barrier and multiple organ failure: role of endotoxin and proinflammatory cytokines in sepsis and necrotizing enterocolitis." J Pediatr Surg 42:454-461.
Neal et al., 2006, "Enterocyte TLR4 mediates phagocytosis and translocation of bacteria across the intestinal barrier." J Immunol 176:3070-3079.
Lee et al., 2006, "Homeostatic effects of TLR9 signaling in experimental colitis." Ann N Y Acad Sci. 1072:351-5.
Obermeier et al. 2002, "CpG motifs of bacterial DNA exacerbate colitis of dextran sulfate sodium-treated mice." Eur J Immunol. Jul. 2002;32(7):2084-92.
Cavallo et al., 2006 "The expression and function of enterocyte toll like receptor-4 are enhanced by lipopolysaccharide in vitro and during systemic endotoxemia." Association for academic surgery and society of university surgeons—Abstracts. Journal of Surgical Researchvol. 130, Issue 2, p. 232, No. 189.
Rachmelewitz et al., 2004, "Toll-like receptor 9 signaling mediates the anti-inflammatory effects of probiotics in murine experimental colitis." Gastroenterology. 126(2):520-8.
Jesse et al., 2006, "Necrotizing enterocolitis: Relationship to Innate Immunity, Clinical Features, and Strategies for Prevention." NeoReviews 7:143-150.
Yang et al., 2005, "Role of Toll-like receptor 4/NF-kappaB pathway in monocyte-endothelial adhesion induced by low shear stress and ox-LDL." Biorheology. 42(3):225-36.
Henry et al., 2006, "Laparotomy Versus Peritoneal Drainage for Perforated Necrotizing Enterocolitis." Neoreviews 7:456-462.
Maeda et al., 2005, "Nod2 mutation in Crohn's disease potentiates NF-kappaB activity and IL-1beta processing." Science 307:734-738. Erratum in Science. Apr. 29, 2005;308(5722):633.
Anderson, 2001, "Infant, neonatal, and postnatal deaths, percent of total deaths, and mortality rates for the 10 leading causes of infant death by race and sex: United States: 1999." National Vital Statistics Reports. 49:73.
Lin et al., 2006, "Necrotising enterocolitis." Lancet 368:1271-1283.
Guthrie et al., 2003, "Necrotizing enterocolitis among neonates in the United States." J Perinatol 23:278-285.
Uauy et al., 1991, "Necrotizing enterocolitis in very low birth weight infants: biodemographic and clinical correlates." National Institute of Child Health and Human Development Neonatal Research Network. J Pediatr 119:630-638.
Gribar et al., 2008, "The role of epithelial Toll-like receptor signaling in the pathogenesis of intestinal inflammation." J Leukoc Biol. 83(3):493-8. Epub Dec. 26, 2007.
Takeda et al., 2001, "Roles of Toll-like receptors in innate immune responses." Genes Cells 6:733-742.
Abreu et al., 2005, "TLR Signaling in the Gut in Health and Disease." J Immunol 174:4453-4460.
Cho et al., 2007, "The genetics of inflammatory bowel disease." Gastroenterology 133:1327-1339.
Kosloske, 1994, "Epidemiology of necrotizing enterocolitis." Acta Pediatr. Suppl. 396:2-7.

Neu et al., 2005, "Intestinal innate immunity: how does it relate to the pathogenesis of necrotizing enterocolitis." Semin. Pediatr. Surg. 14: 137-144.

Moss et al., 2006, "Laparotomy versus peritoneal drainage for necrotizing enterocolitis and perforation." N. Engl. J. Med. 354:2225-2234.

Halpern et al., "Reduction of experimental necrotizing enterocolitis with anti-TNF-alpha", Am J Physiol Gastrointest Liver Physiol 290:757-764, 2006, First published Nov. 3, 2005, entire document especially abstract; p. 1.

Grimm et al., "NOD2 Mutations and Crohn's Disease: Are Paneth Cells and Their Antimicrobial Peptides The Link?" Gut; 53(11): 1558-1560, Nov. 2004, entire document especially p. 2.

Daubenberger, 2007, "TLR9 agonists as adjuvants for prophylactic and therapeutic vaccines." Curr. Opin. Molec. Ther. 9:45-52.

Krieg, 2006, "Therapeutic potential of Toll-like receptor 9 activation." Nat. Rev. Drug Disc. 5:471-484.

Macagno et al., 2006, "A cyanobacterial LPS antagonist prevents endotoxin shock and blocks sustained TLR4 stimulation required for cytokine expression." J. Exp. Med. 203(6):1481-1492.

InvivoGen: Delivering Genes. "TLR9 Ligands." Downloaded on Apr. 16, 2007 from hrrp://www.invivogen.com/family.php?ID=104&ID_cat=2&ID_sscat=9.

Vink et al., 2002, "In vivo evidence for a role of toll-like receptor 4 in the development of intimal lesions." Circulation. 106(15):1985-90.

Strober et al., 2006, "Signalling pathways and molecular interactions of NOD1 and NOD2." Nat Rev Immunol. 6:9-20.

Creagh et al., 2006, "TLRs, NLRs and RLRs: a trinity of pathogen sensors that co-operate in innate immunity." Trends Immunol. 27(8):352-7. Epub Jun. 27, 2006.

Pierro, 2005, "The surgical management of necrotising enterocolitis." Early Hum Dev. 81(1):79-85.

Poltorak et al., 1998, "Defective LPS Signaling in C3H/HeJ and C57BL/10ScCr Mice: Mutations in T1r4 Gene." Science 282: 2085-2088.

Takeda et al., "Toll-like receptors in innate immunity." Int Immunol. 17(1):1-14, 2005.

U.S. Appl. No. 12/104,816, Jan. 23, 2012 Notice of Allowance.

U.S. Appl. No. 12/104,816, Apr. 23, 2012 Issue Fee payment.

U.S. Appl. No. 13/461,672, Jan. 14, 2013 Non-Final Office Action.

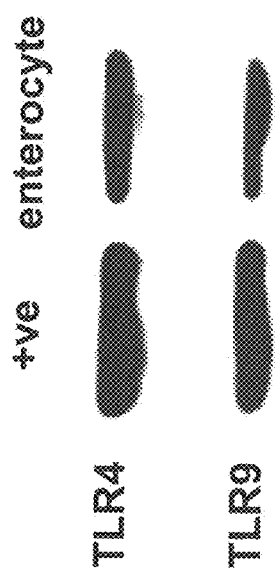

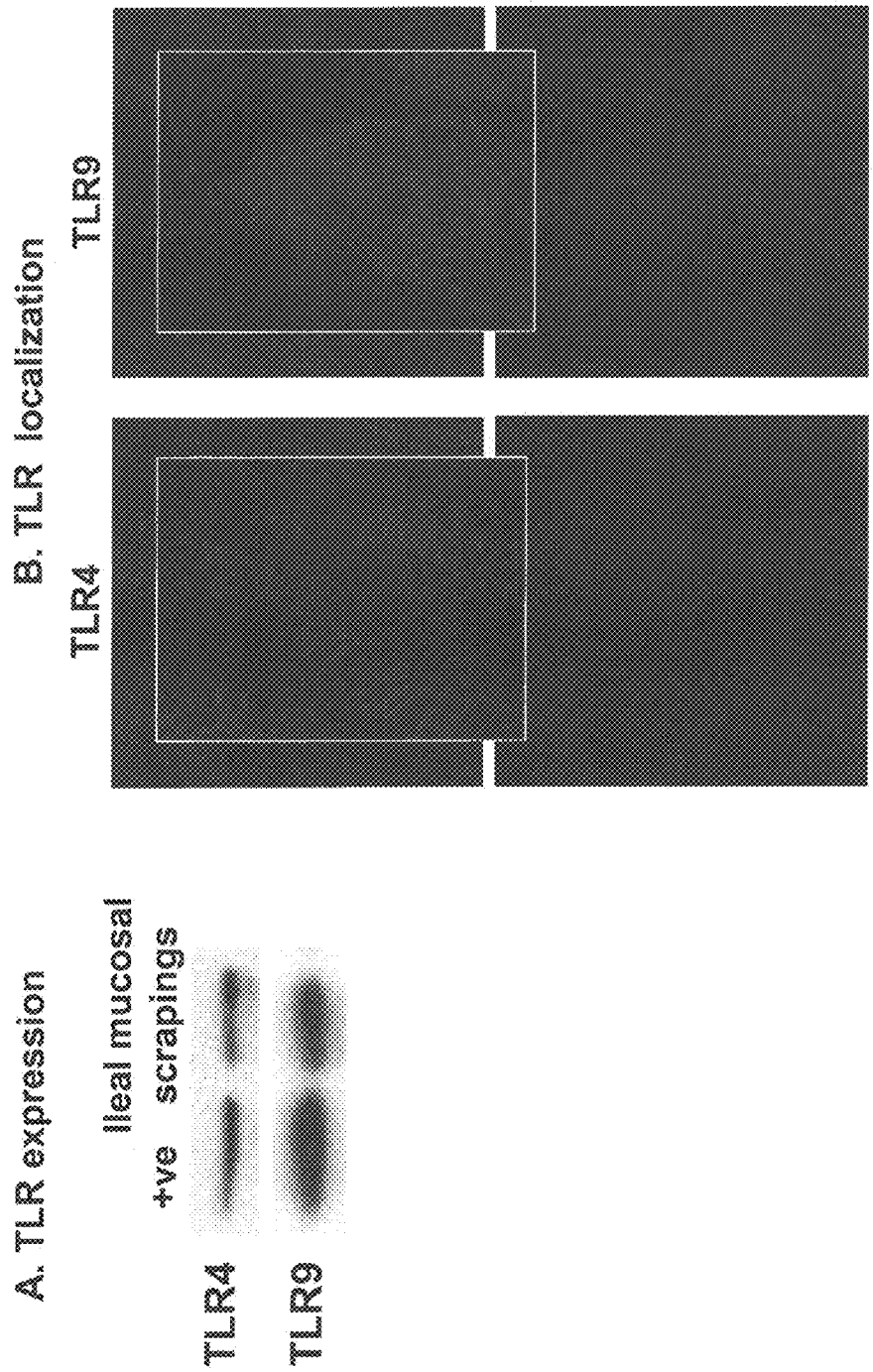
Figure 2A-B

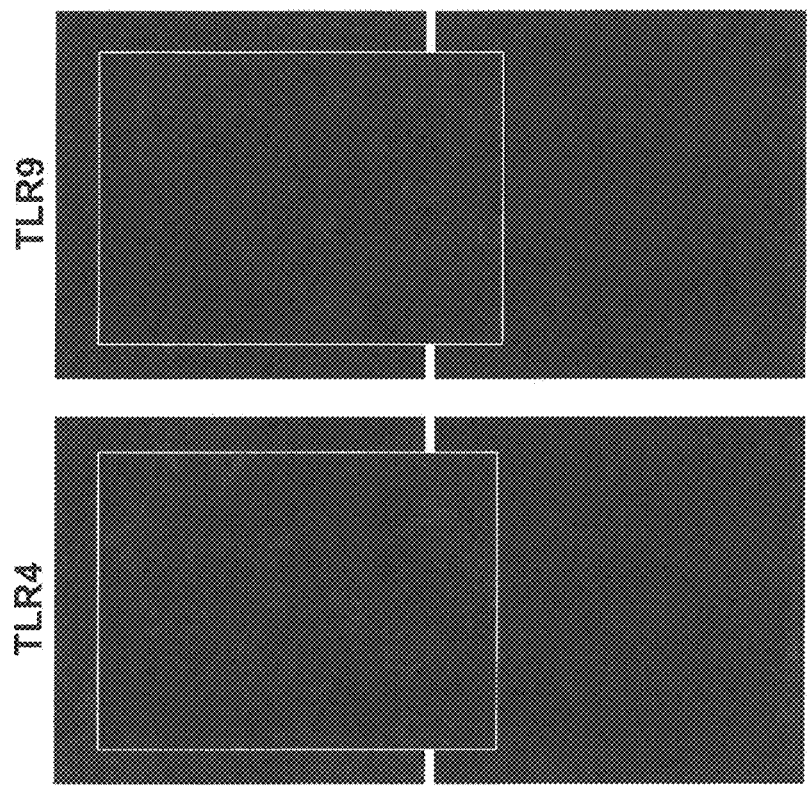

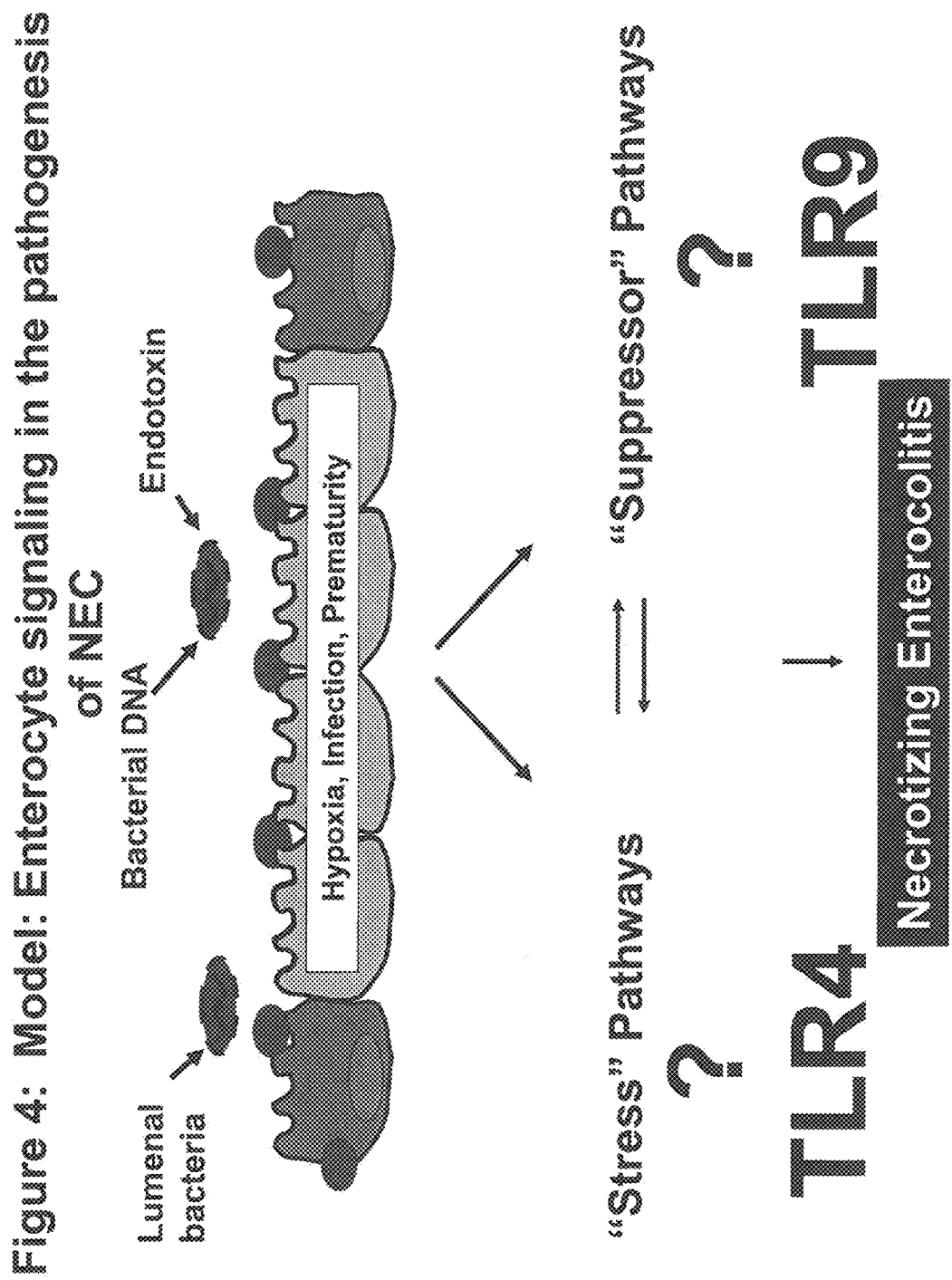

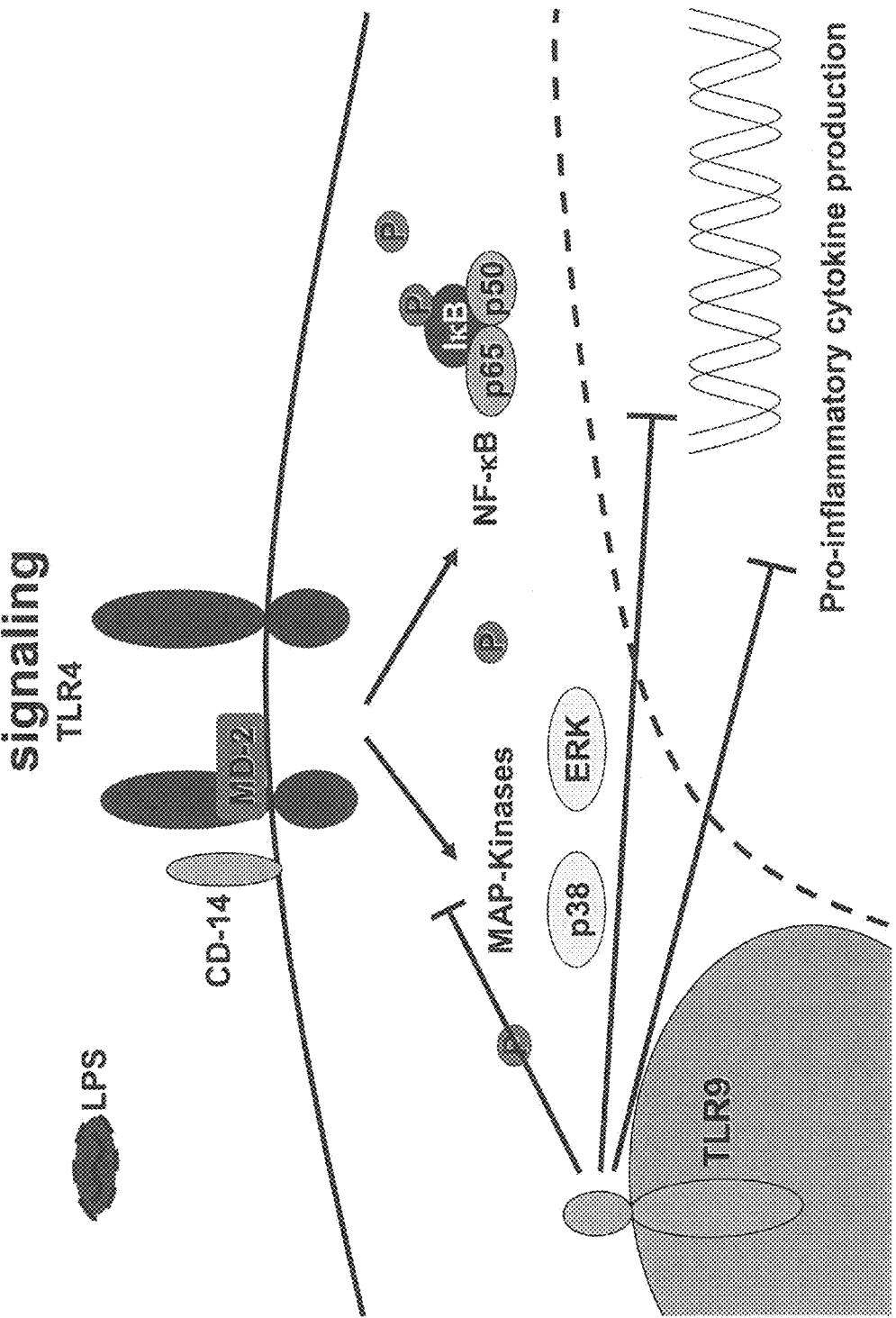

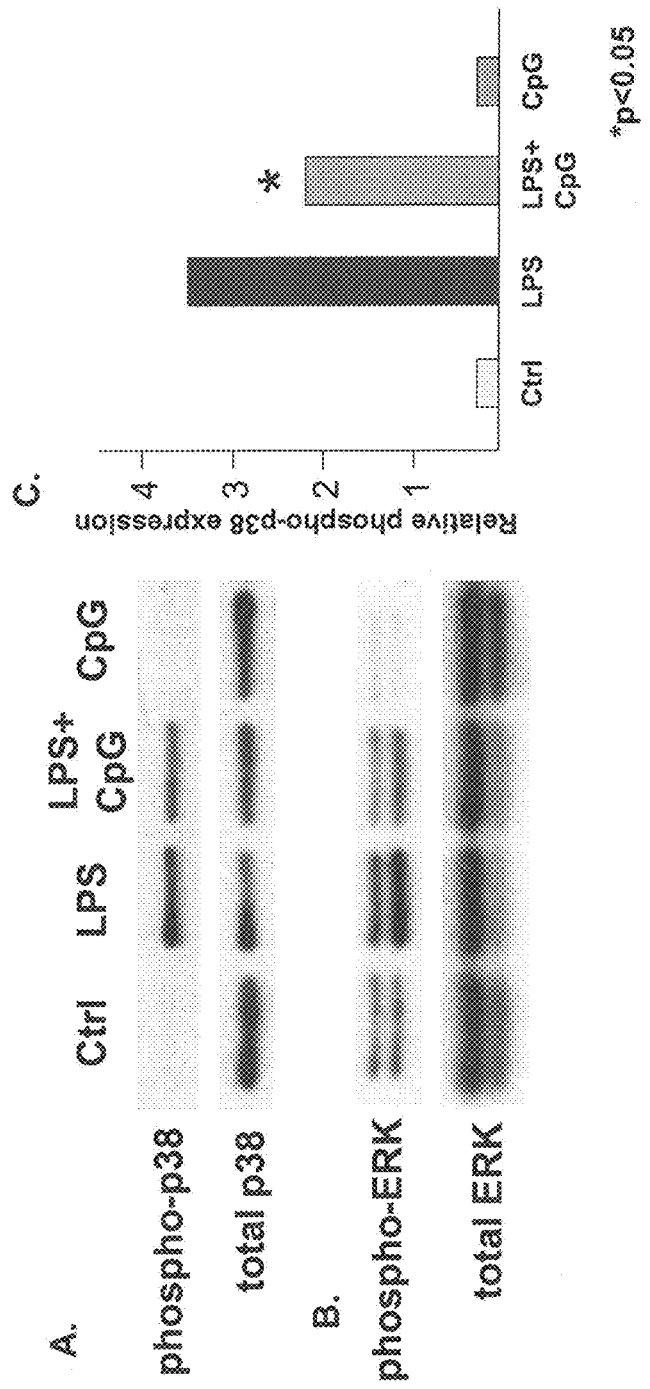

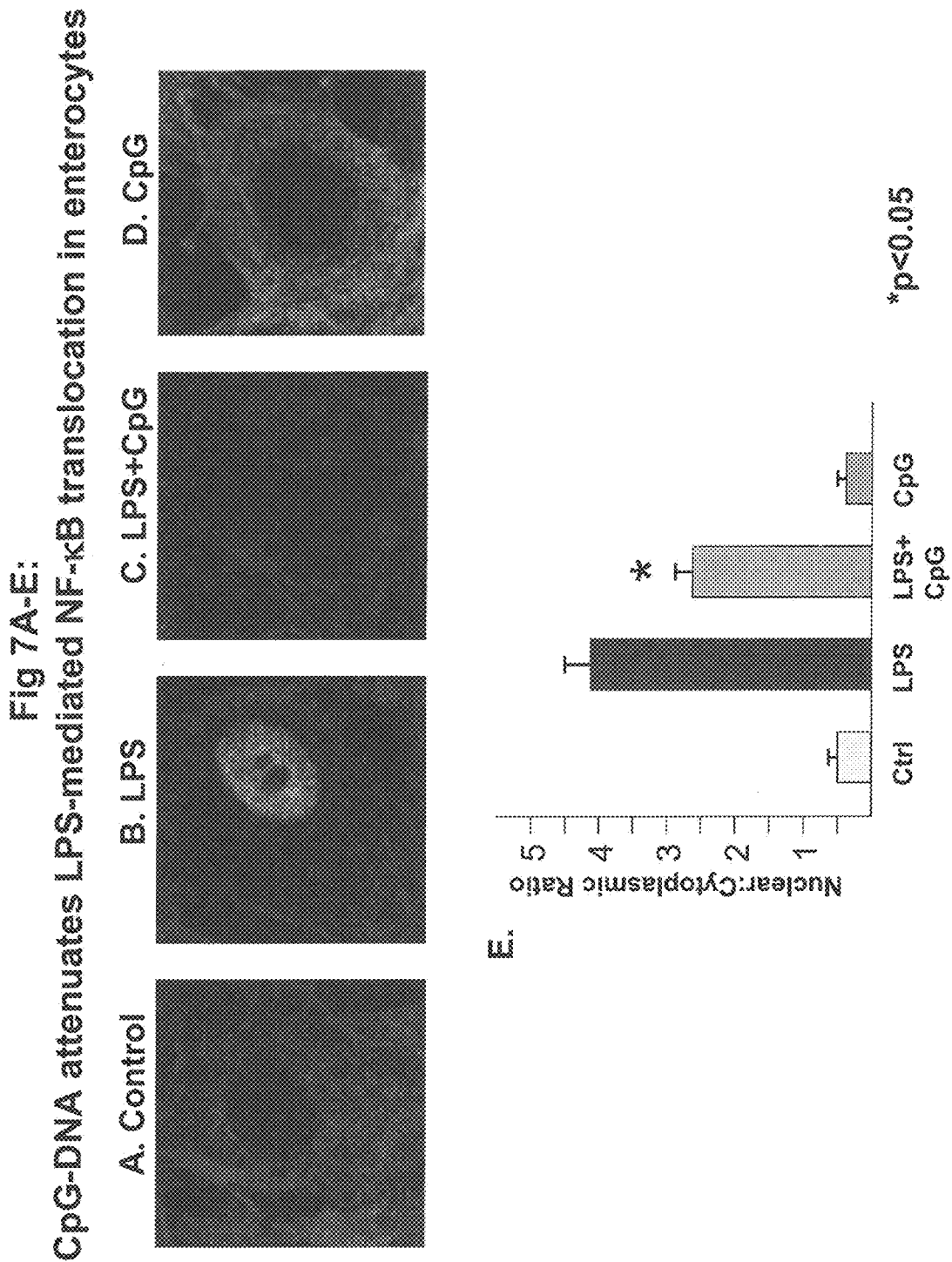
Fig 7A-E:
CpG-DNA attenuates LPS-mediated NF-κB translocation in enterocytes

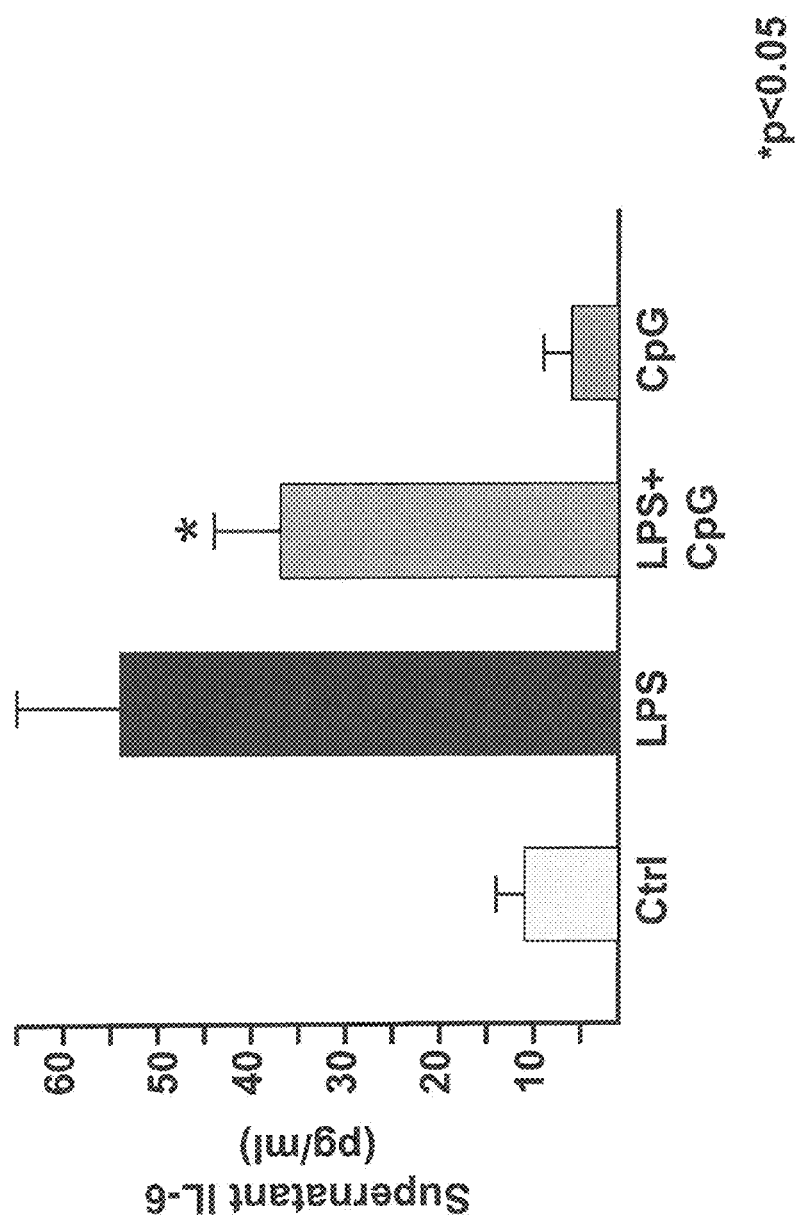

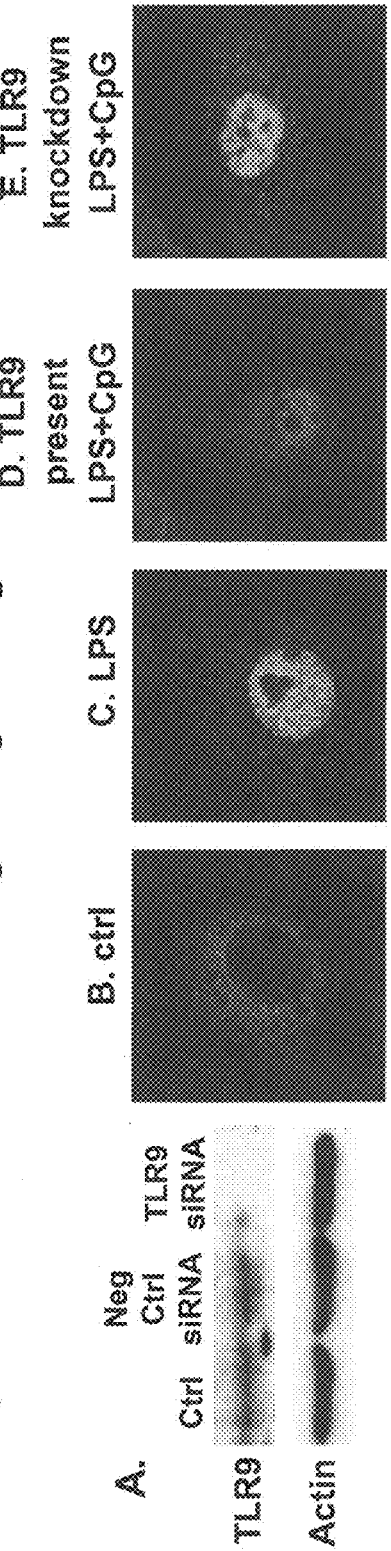
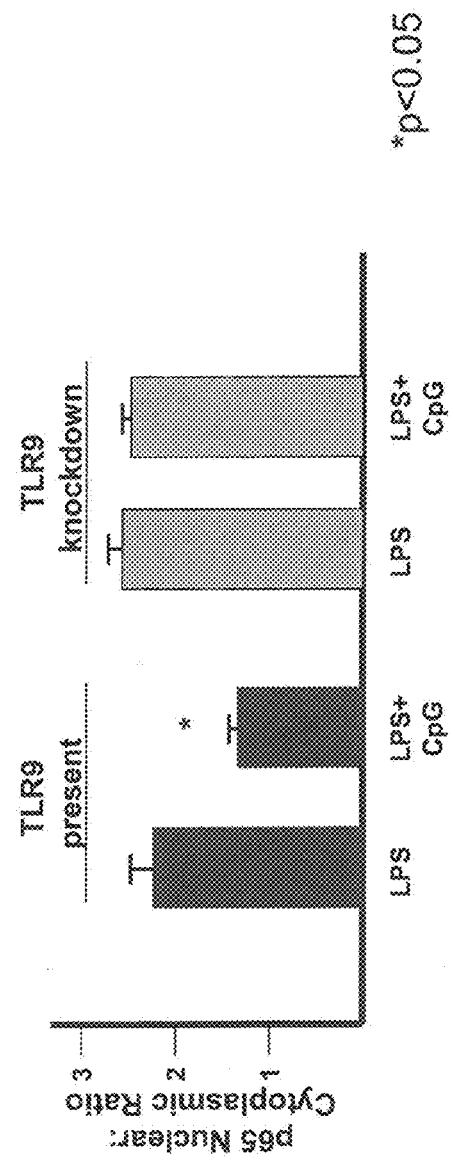
Figure 9A-F
CpG-DNA reduces TLR4 signaling through TLR9 in enterocytes

Figure 10: Does TLR9 activation affect TLR4-mediated inflammation in vivo?

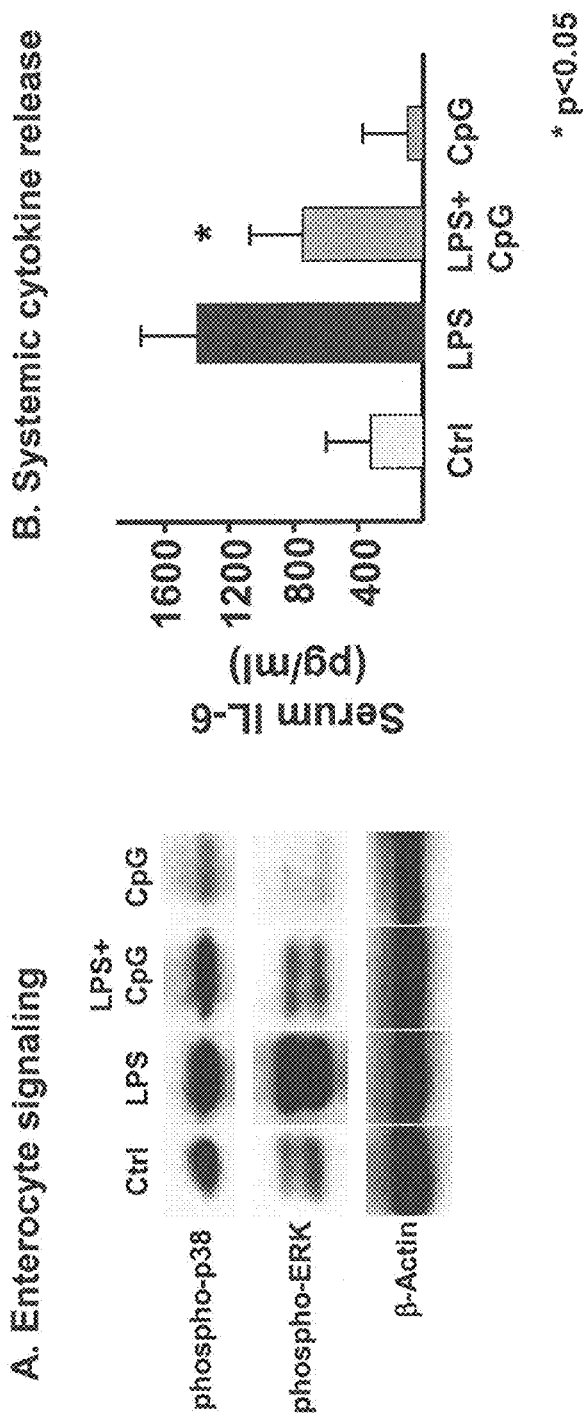
Figure 11A-B LPS-dependent signaling and inflammation is attenuated by CpG-DNA in the intestinal mucosa

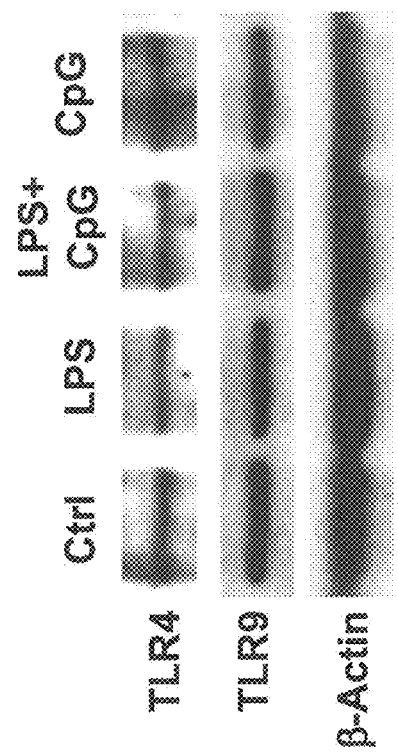
Figure 12: TLR4 and TLR9 expression are unchanged by CpG-DNA and LPS in enterocytes

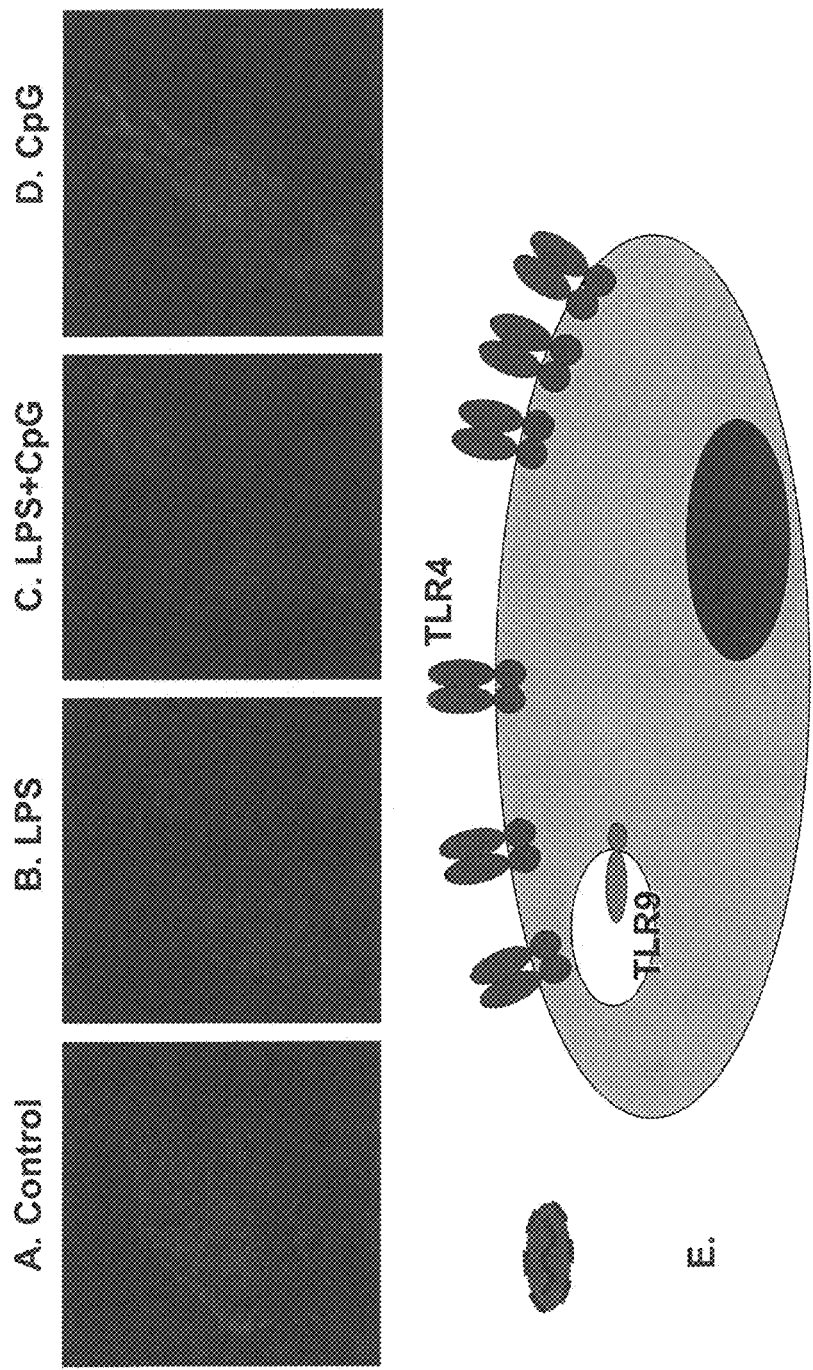
Figure 13A-E CpG-DNA causes a redistribution of TLR4 into internal structures IEC-6 cells

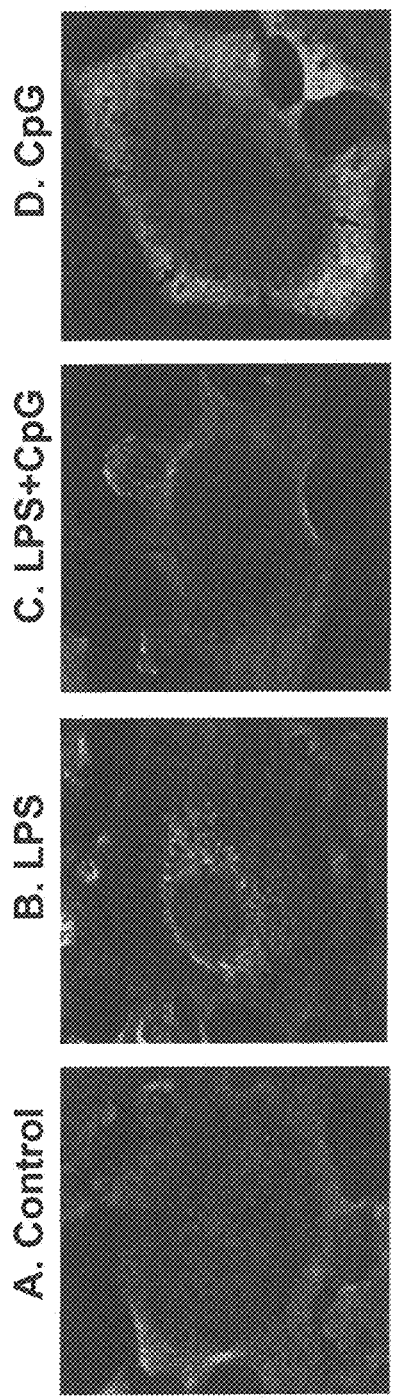
Figure 14A-D: LPS causes the internalization of TLR9, which is reversed by CpG-DNA

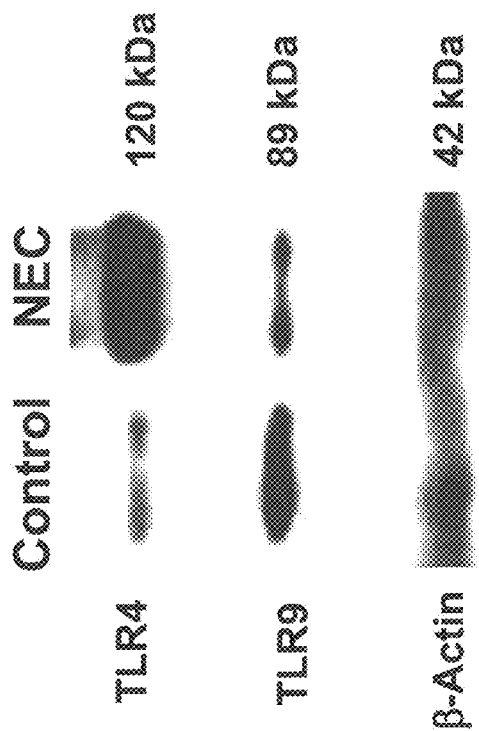
Figure 16: A role for TLR4 and TLR9 in NEC

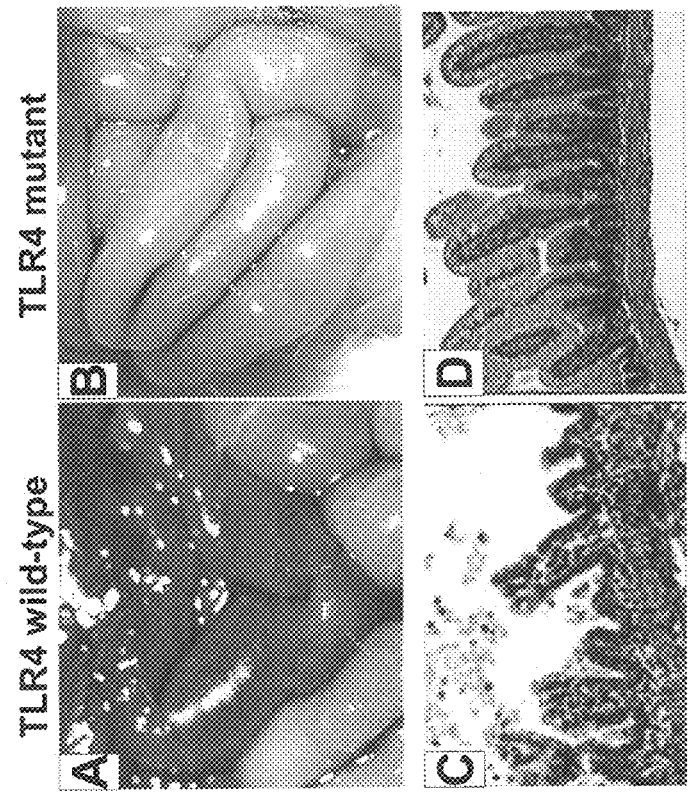
Figure 17A-D

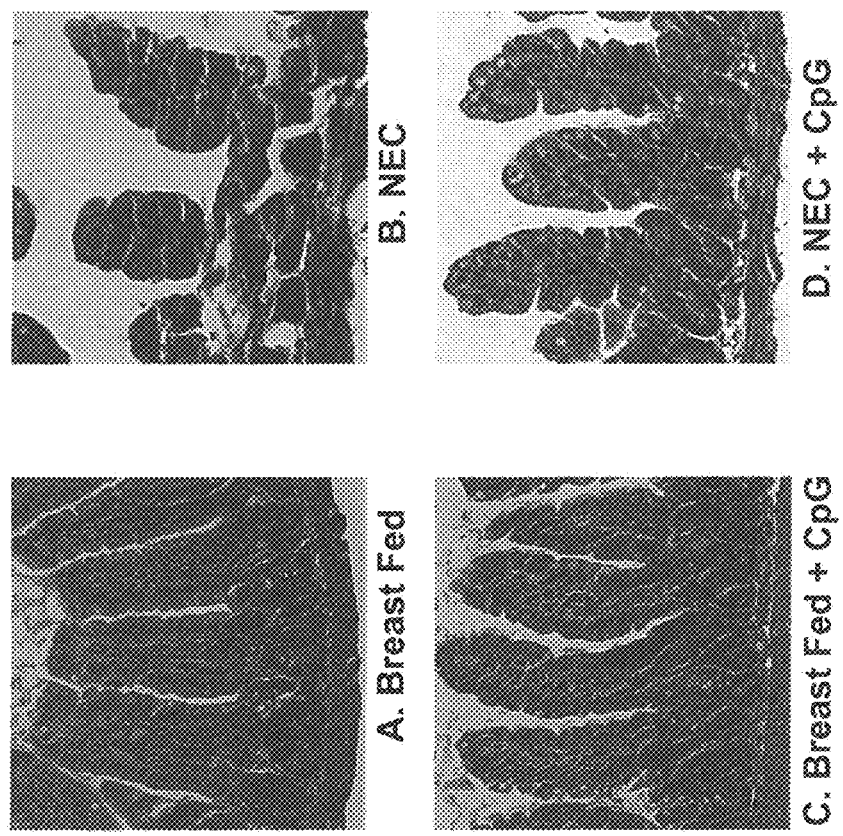
Figure 18A-D

Figure 19A-C
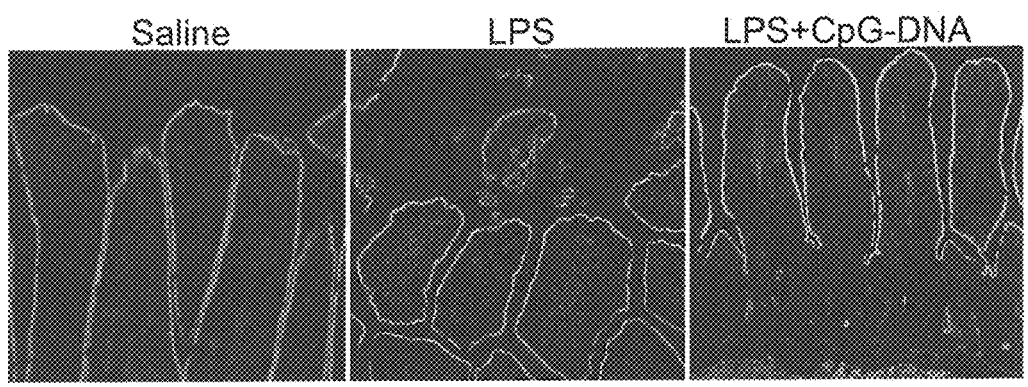

Figure 19D-H
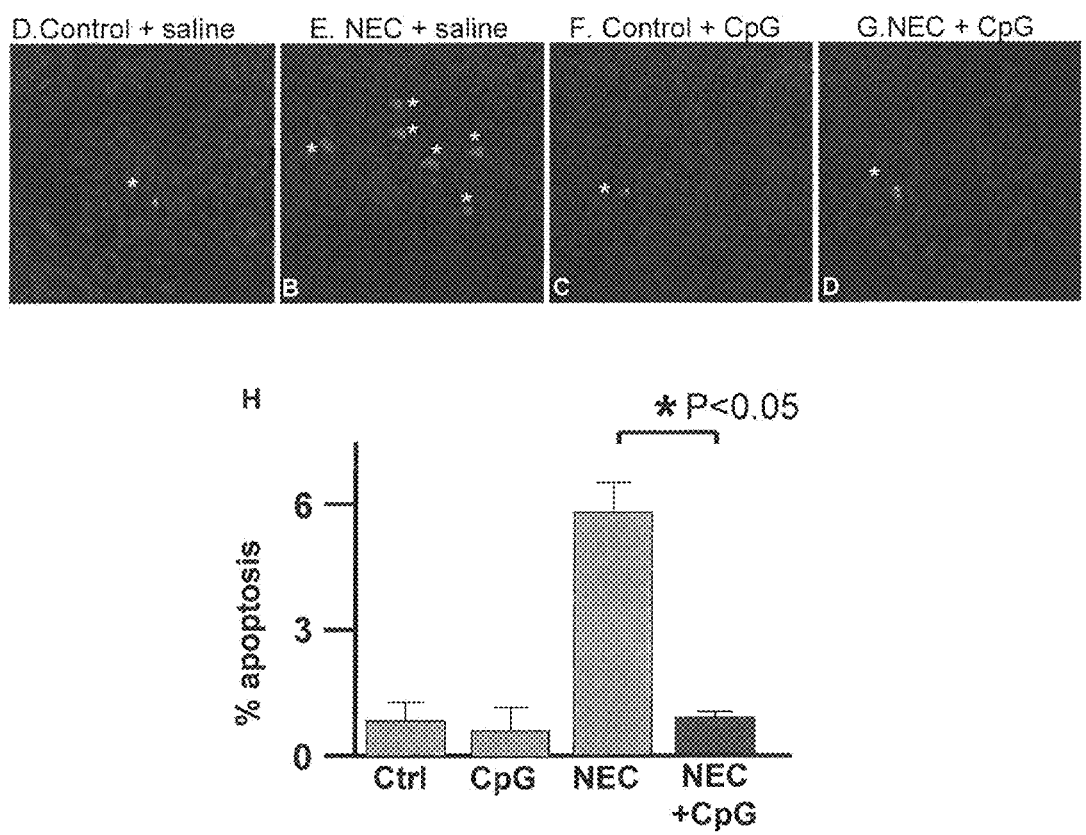

Figure 20A-I
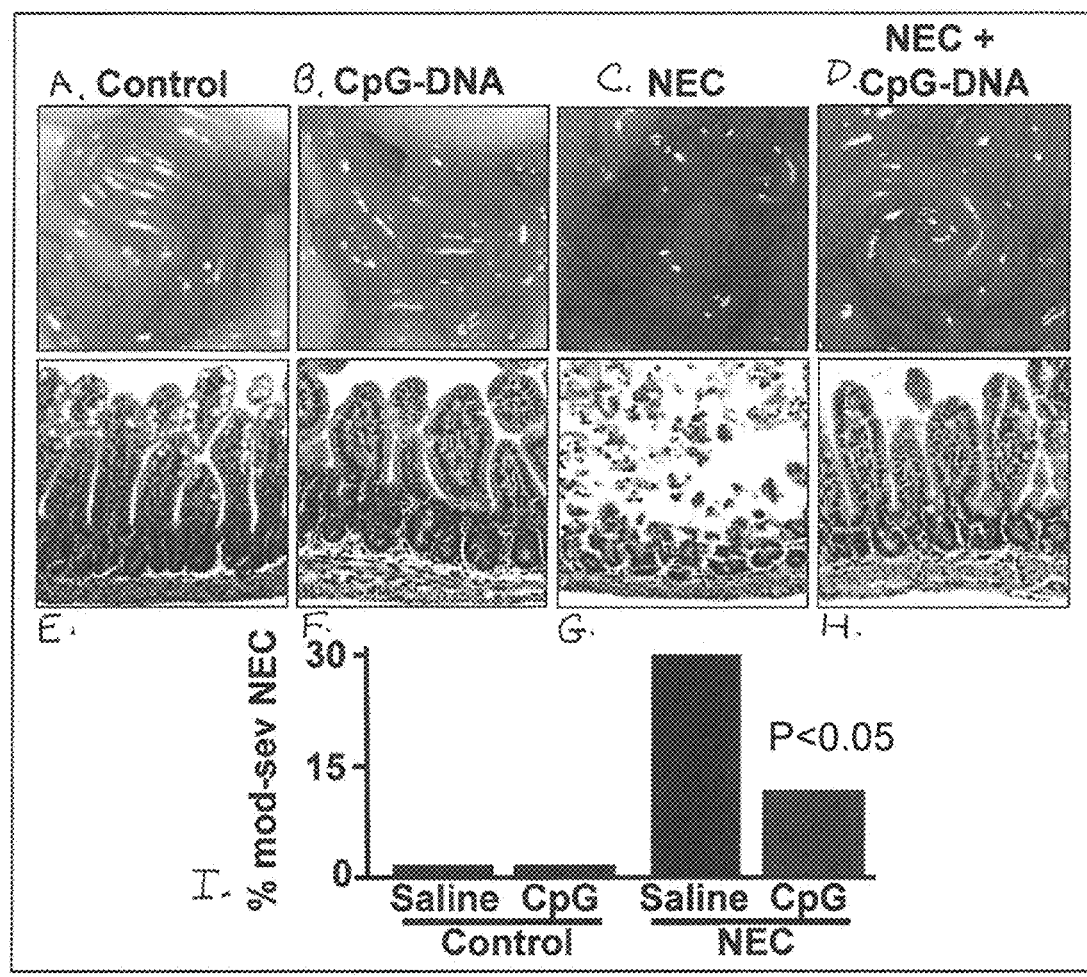

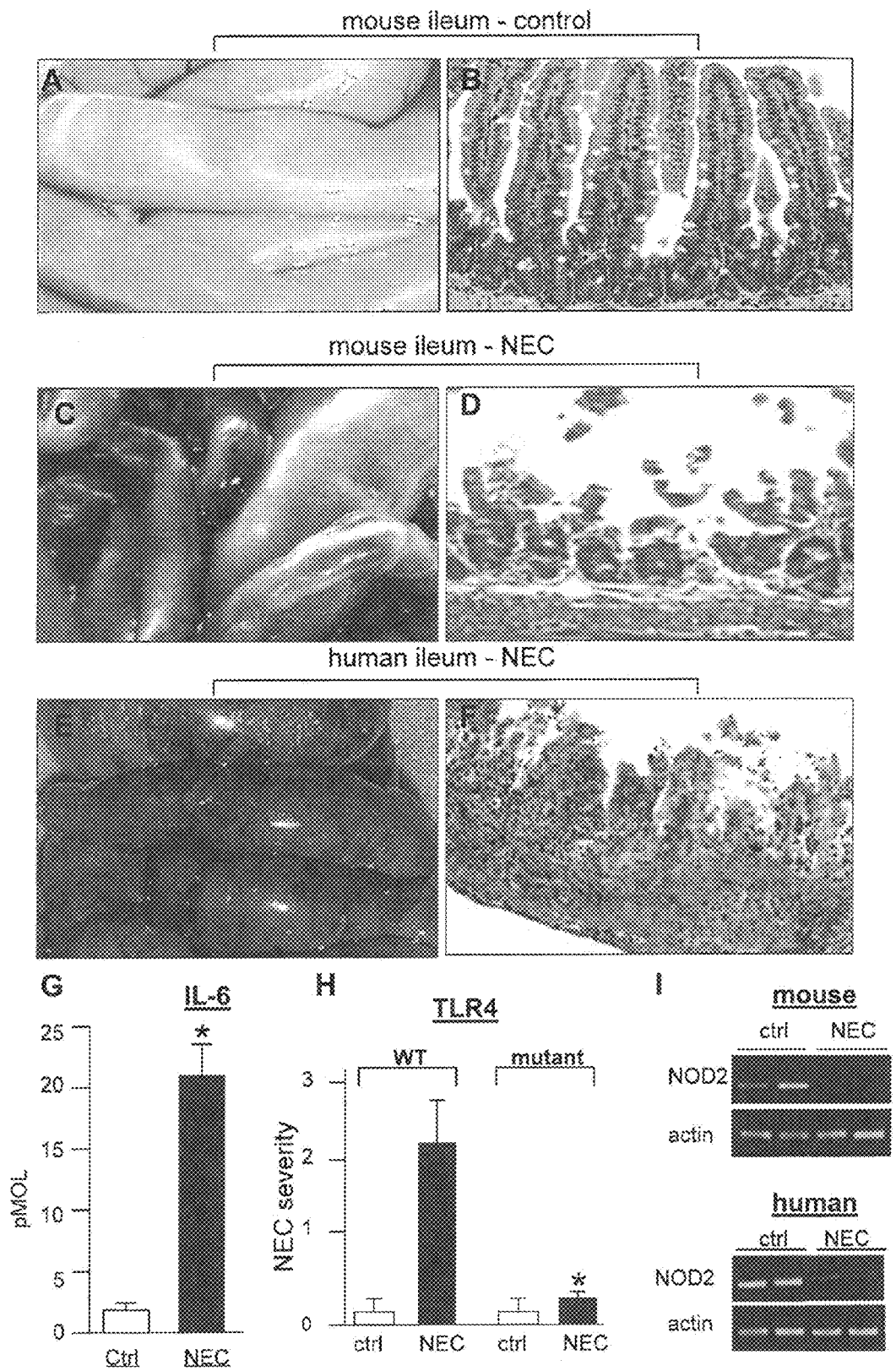
Figure 22 A-G. Experimental NEC. H: TLR4 is required for NEC. I: NOD2 is reduced in NEC.

FIGURE 23A-E
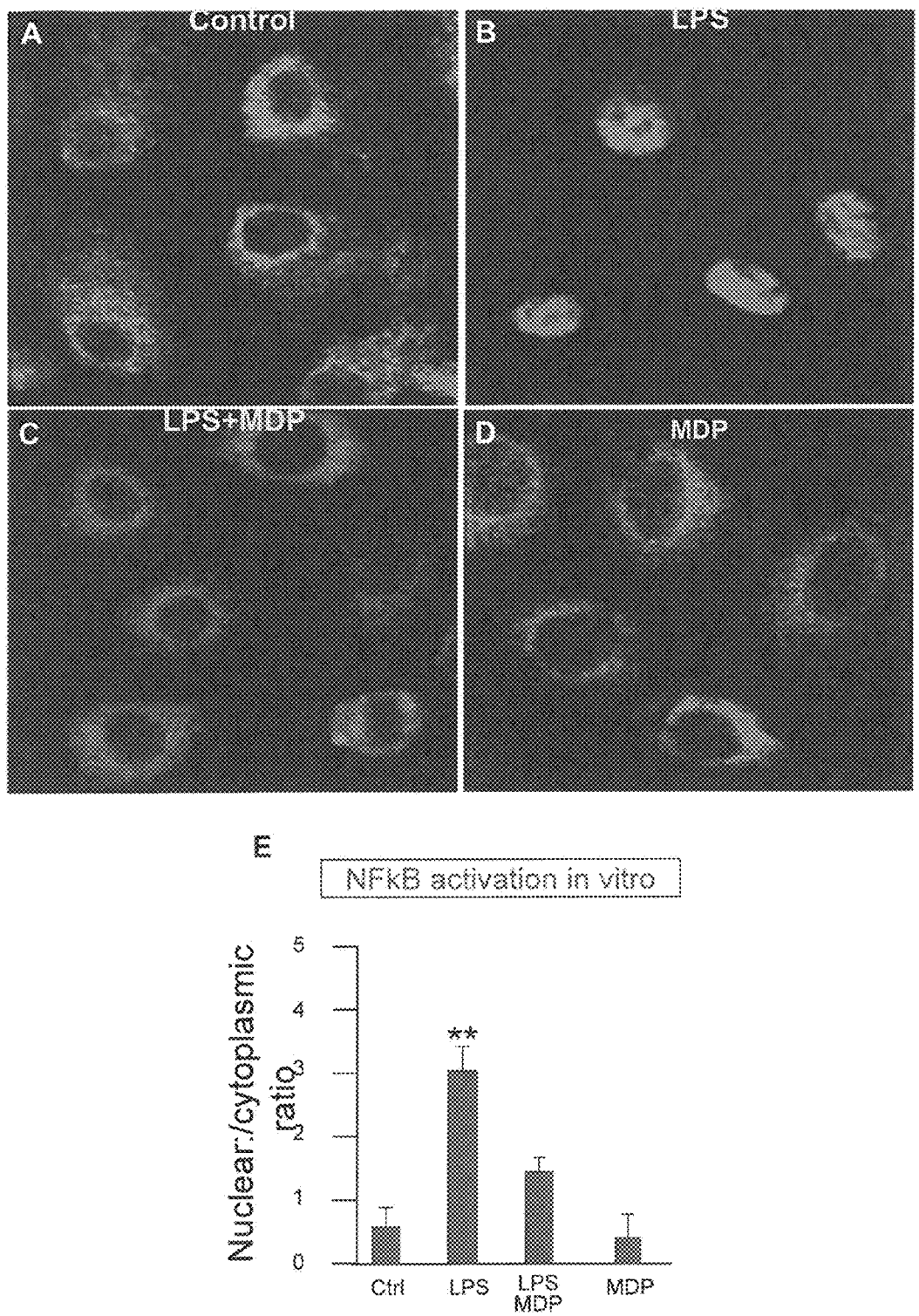

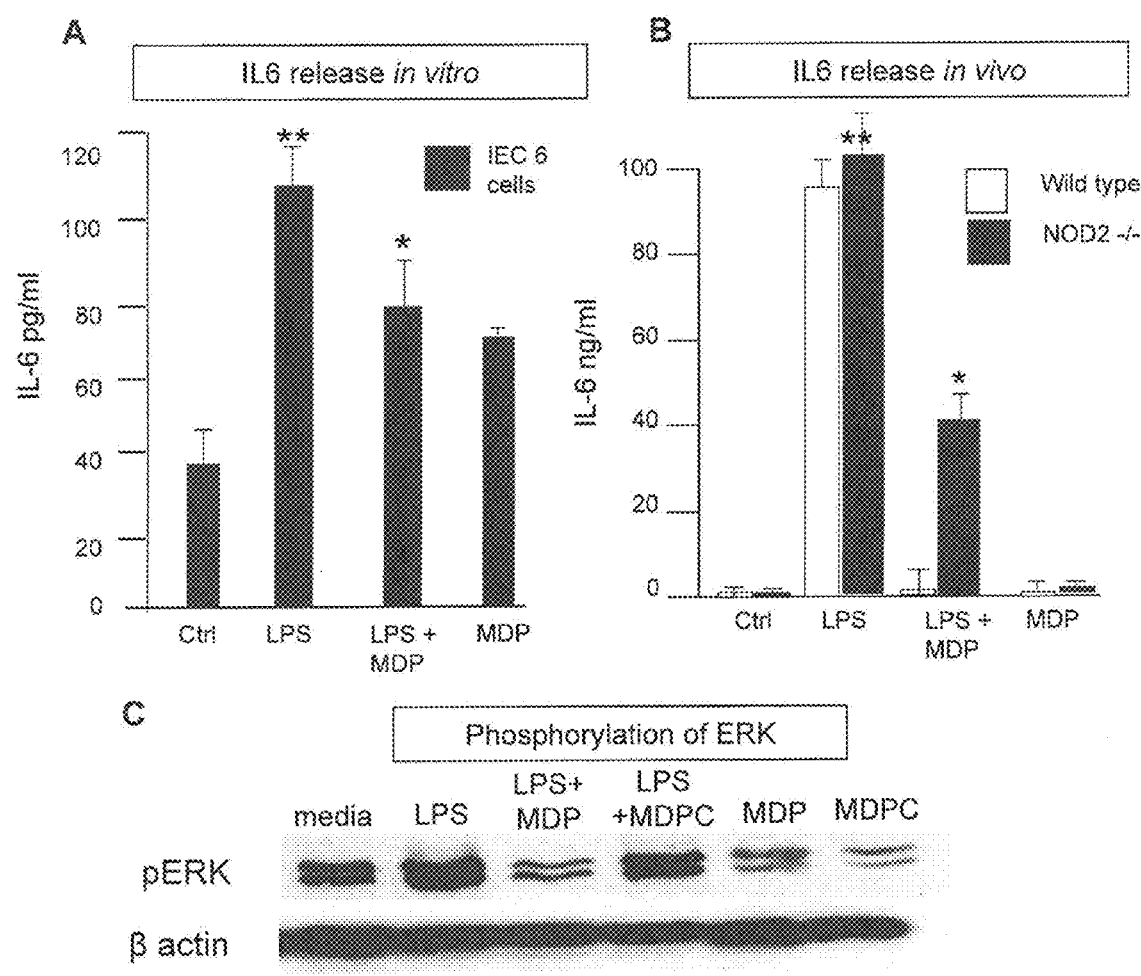
Figure 24A-C

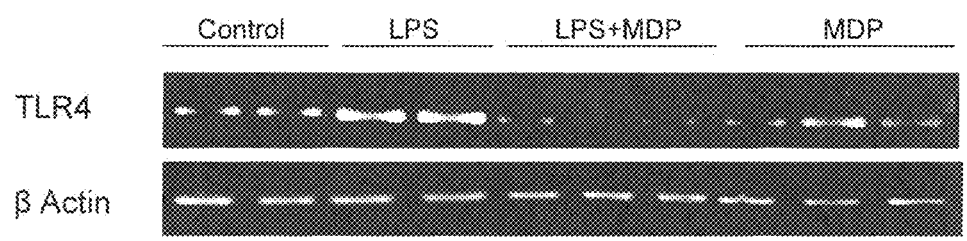
Figure 25. NOD2 Activation decreases TLR4 expression in vivo

Figure 26A-E
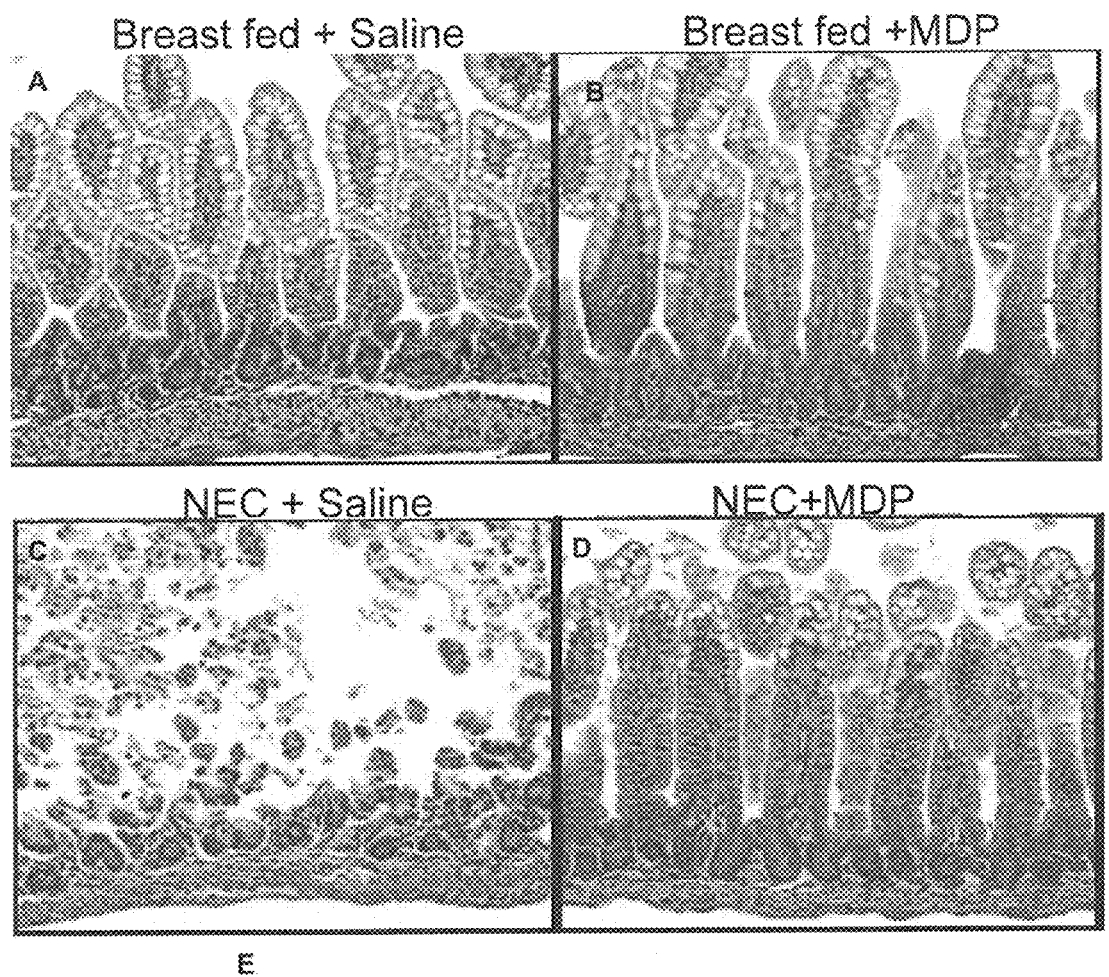
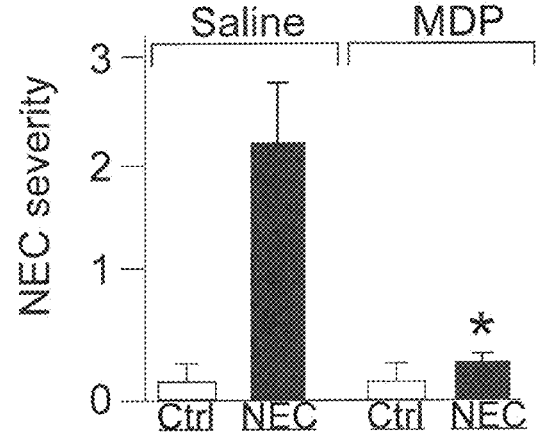

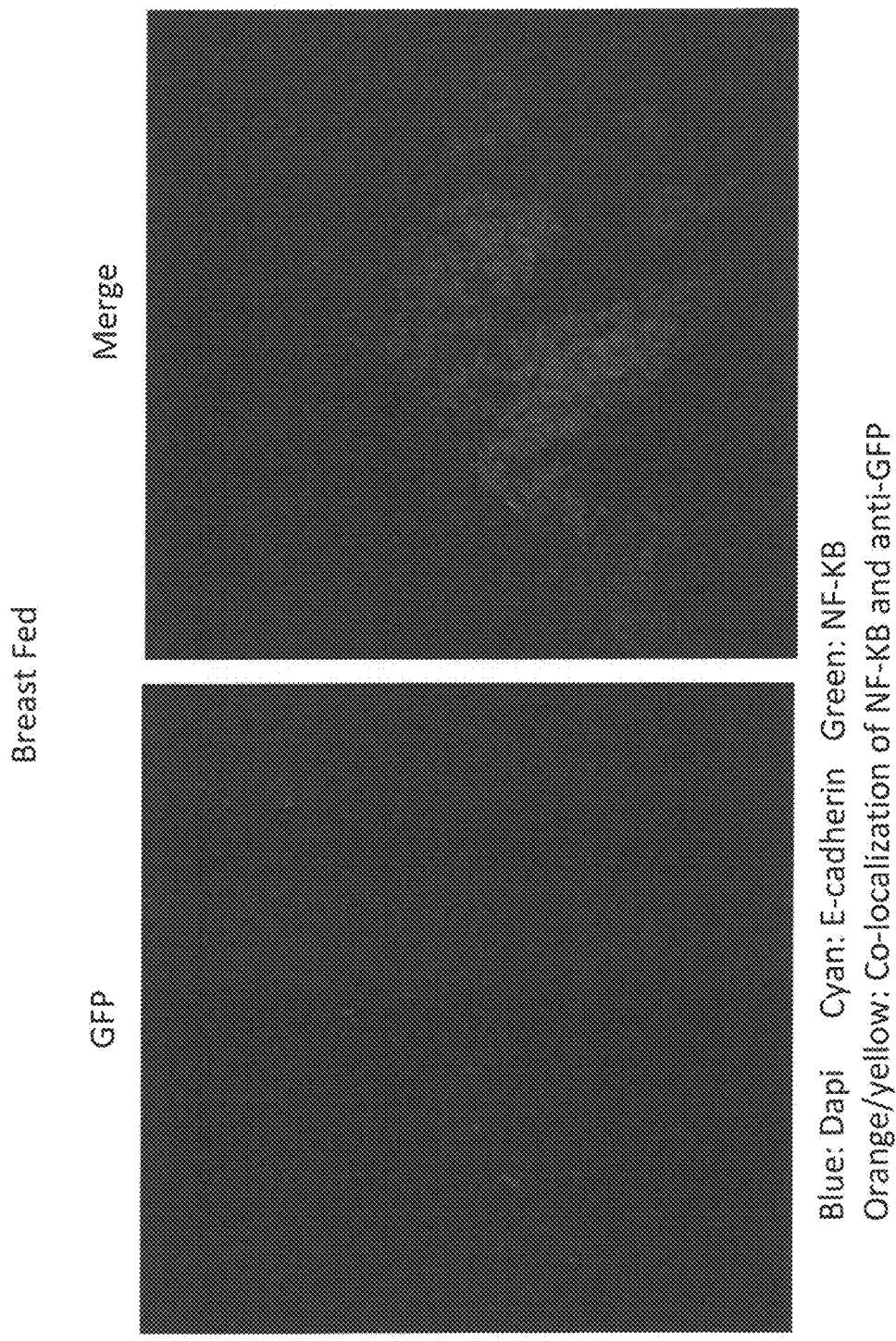

USE OF TOLL-LIKE RECEPTOR-9 AGONISTS

CROSS-REFERENCE TO RELATED APPLICATIONS

This application is a continuation in part of U.S. Ser. No. 12/104,816, filed Apr. 17, 2008, which claims priority to U.S. Provisional Application Ser. No. 61/027,728, filed Feb. 11, 2008, and to U.S. Provisional Application Ser. No. 60/912,862, filed Apr. 19, 2007. This application also claims priority to U.S. Provisional Application Ser. No. 61/334,999, filed May 14, 2010. Each of the foregoing applications are hereby incorporated by reference in their entireties.

GRANT INFORMATION

The TLR4 and TLR9-related subject matter of this application was made with government support under Grant No. R01-GM078238-01 awarded by the National Institutes of Health. The United States Government has certain rights in the invention. No federal funds were used in the development of subject matter related to NOD2.

1. INTRODUCTION

The present invention relates to the use of a Toll-like receptor-9 (TLR9) agonist and/or a Toll-like receptor-4 (TLR4) antagonist and/or a Nuclear Oligomerization Domain-2 (NOD2) agonist for treatment or prevention of disorders involving Toll-like receptor-4 (TLR4) activation, such as systemic sepsis and necrotizing enterocolitis. It is based, at least in part, on the discovery that a TLR9 agonist, a TLR4 antagonist, and a NOD2 agonist can suppress the consequences of TLR4 activation in such conditions.

SEQUENCE LISTING

The specification further incorporates by reference the Sequence Listing submitted herewith via EFS on Dec. 5, 2011. Pursuant to 37 C.F.R. §1.52(e)(5), the Sequence Listing text file, identified as 0723960438SeqUst.txt, is 4,484 bytes and was created on Dec. 5, 2011. The Sequence Listing, electronically filed herewith, does not extend beyond the scope of the specification and thus does not contain new matter.

2. BACKGROUND OF THE INVENTION

2.1 Necrotizing Enterocolitis

Necrotizing enterocolitis ("NEC") is the most common—and most lethal—disease affecting the gastrointestinal tract of premature infants. It has become more common as the survival rate of premature infants has improved, and is diagnosed at an incidence of between 0.09 and 0.24 percent of live births (Feng et al., 2005, Semin. Pediatr. Surg. 14:167-174; Henry et al., 2005, Semin. Pediatr. Surg. 14: 181-190; Warner et al., 2005, Semin. Pediatr. Surg. 14: 181-190; Hsueh et al., 2003, Pediatr. Dev. Pathol. 6: 6-23). Risk factors for NEC include (in addition to prematurity), aggressive enteral feeding, episodes of birth asphyxia, polycythemia, umbilical vessel catheterization, congenital heart disease, hyperosmolar nutritional formulas, maternal cocaine use, respiratory distress syndrome, and maternal preeclampsia (Anand et al., 2007, Shock 27(2):124-133, citing Hsueh et al., 2003, Pediatr. Dev. Pathol. 6: 6-23; Neu, 1996, Pediatr. Clin. N. Am. 43: 409-432; Kosloske, 1994, Acta Pediatr. Suppl. 396:2-7; Neu et al., 2005, Semin. Pediatr. Surg. 14: 137-144; Shin et al., 2000, J. Pediatr. Surg. 35: 173-176; Ng, 2001, J. Paediatr Child Health 37:1-4). In more advanced instances of the disease, it may result in intestinal necrosis and perforation, multisystem organ failure, systemic sepsis, and death.

Evidence suggests that the pathogenesis of NEC involves aberrant bacterial-enterocyte signaling. A role for gram negative bacteria in the pathogenesis of NEC is supported by the observations that NEC cases often occur in epidemic outbreaks, NEC responds to systemic antibiotics, patients with NEC are frequently found to have positive blood cultures for enteric organisms, and there are markedly increased serum levels of lipopolysaccharide ("LPS") in patients with NEC. It has been hypothesized that an episode of systemic stress leads to translocation of bacteria across the intestinal barrier, to result in activation of stress pathways and of the immune system, resulting in a global inflammatory response and tissue injury (Anand et al., 2007, Shock 27(2):124-133).

Treatment of NEC involves, first, supportive therapy in the form of nasogastric decompression and resuscitation with isotonic solutions. In addition, broad spectrum antibiotics are administered. More severe cases are further managed with operative intervention, including removal of necrotic intestine and creation of stomas. The mortality associated with NEC, particularly if intestinal perforation has occurred, is high, and has been set at between 20 and 50 percent (Henry and Moss, 2006, NeoRev. 7(9): e456). In infants having a birth weight of less than 1500 g, with a perforated intestine, despite treatment a mortality of approximately 35 percent was recently observed (Moss et al., 2006, N. Engl. J. Med. 354:2225-2234).

2.2 TLRs

Bacterial signaling occurs via Toll-like receptors ("TLRs") in the intestine. TLRs participate in what is referred to as the "innate immune response" and play both activating and inhibitory roles.

Gram negative bacteria and their products are known to interact with TLR4 and TLR9. TLR4, which is activated by LPS, has been reported to be expressed on the apical surface of enterocytes and to bind and internalize purified endotoxin (Cetin et al., 2004, J. Biol. Chem. 279:24592-24600; Cario et al., 2000, J. Immunol. 164:966-972; Otte et al., 2004, Gastroenterol. 126:1054-1070). TLR 4 has also been implicated in phagocytosis and translocation of bacteria across the intestinal barrier (Neal et al., 2006, J. Immunol. 176:3070-3079). TLR9 has been reported to be expressed on the colonic apical surface in wildtype, but not germ-free, mice, suggesting that expression of TLR9 in these cells may be upregulated in response to pathogenic bacterial DNA (Ewaschuk et al., 2007, Inf. & Immun., published online ahead of print, doi: 10.1128/IAI.01662-06).

Activating TLR9 ligands, CpG oligonucleotodies (CpG ODNs) are disclosed as useful in treating inflammatory bowel disease (see U.S. Pat. No. 6,613,751, Lee et al., 2006, Ann. N.Y. Acad. Sci. 1072:351-355; Katakura et al., 2005, J. Clin. Invest. 115:695) and in lipopolysaccharide (LPS)-associated disorders (see U.S. Pat. No. 6,214,806). However, the association, according to the present invention, between TLR9 activation and TLR4 inhibition had not hitherto been made, nor had the use of TLR9 activation in the treatment of necrotizing enterocolitis been known.

2.3 NOD2

A novel arm of the enterocyte innate immune system governed by nucleotide oligomerization domain-2 (NOD2) has recently been identified. NOD2 is a member of the NOD Like Receptors (NLR) family of cytoplasmic pathogen recognition receptors that detect bacterial motifs, in particular the bacterial cell wall component muramyl-di-peptide (MDP) (Kanneganti and Núñez, 2008, Immunity 27:549-559). The importance of NOD2 signaling and the development of intestinal inflammation was confirmed as mutations in the NOD2 gene were found to be increased in a large cohort of patients with Crohn's disease, a chronic intestinal inflammatory disorder (Carneiro et al., 2008, J. Pathol. 214:136-148; Franchi et al., 2008, Cell Microbiol 10:1-8).

3. SUMMARY OF THE INVENTION

The present invention relates to the use of a TLR9 agonist and/or a TLR4 antagonist and/or a NOD2 agonist for treatment or prevention of disorders involving TLR4 activation, such as systemic sepsis and NEC. The TLR9-related aspect of the present invention is based, at least in part, on the discovery that activation of TLR9 inhibited TLR4 signaling in enterocytes in vitro and in vivo, leading to a reduction in indicia of inflammation. The TLR4-related aspect of the present invention is based, at least in part, on the discovery that NFκB activation, inhibited by a TLR9 agonist, could be further inhibited by a TLR4 antagonist. The NOD2-related aspect of the present invention is based, at least in part, on the discovery that (i) experimental and human NEC are associated with the loss of NOD2 expression in the intestinal mucosa, (ii) activation of NOD2 with the specific agonist muramyl-di-peptide (MDP) led to a reduction in TLR4-mediated signaling in enterocytes, and (iii) administration of MDP to newborn mice in an experimental model of NEC conferred significant protection against the development of NEC.

Accordingly, the present invention provides for methods and compositions for treating or preventing disorders associated with TLR4 activation, in particular disorders epidemiologically linked to bacterial endotoxin, by administering an effective amount of an agonist of TLR9 and/or an effective amount of an agonist of NOD2. In a subset of non-limiting embodiments, one or more agonist of TLR9 and/or one or more agonist of NOD2 may be administered together with an antagonist of TLR4.

In specific, non-limiting embodiments, the present invention provides for methods comprising administering, to an infant (for example, a premature infant or a term infant otherwise at risk for the disease), an effective amount of an agonist of NOD2, such as but not limited to muramyl-di-peptide, which reduces the risk of the infant developing NEC. Such methods may further comprise administering an effective amount of an agonist of TLR9 and/or an antagonist of TLR4. In related embodiments, the present invention provides for pharmaceutical compositions, including nutritional formulations, comprising effective concentrations of NOD2 agonist which optionally further comprise one or more TLR9 agonist and/or one or more TLR4 antagonist.

In further specific, non-limiting embodiments, the present invention provides for methods of treating NEC, including reducing the severity of NEC, in an infant suffering from the disease, comprising administering to the infant an effective amount of an agonist of NOD2, such as but not limited to muramyl-di-peptide. Such methods may further comprise administering an effective amount of an agonist of TLR9 and/or an antagonist of TLR4.

4. BRIEF DESCRIPTION OF THE FIGURES

The patent or application file contains at least one drawing executed in color. Copies of the patent or patent application publication with color drawing(s) will be provided by the Office upon request and payment of the necessary fee.

FIG. 1. Western blot showing expression of TLR4 and TLR9 in positive control cells and enterocytes.

FIG. 2A-B. TLR4 and TLR9 are expressed on the murine intestine. (A) Western blot showing expression of TLR4 and TLR9 in positive control cells and in murine ileal mucosal scrapings. (B) Immunofluorescence studies showing expression of TLR4 and TLR9 in murine intestine.

FIG. 3. Immunofluorescence studies showing expression of TLR4 and TLR9 in the intestine of human neonates.

FIG. 4. Schematic diagram of a model for the etiology of NEC, where, in the context of physiologic stressors such as hypoxia, infection, and/or prematurity, bacterial DNA and endotoxin from lumenal bacteria can activate TLR4 as well as suppressor pathways involving TLR9.

FIG. 5. Schematic diagram of the various molecules involved in the (indirect) interactions between TLR9 and TLR4 which may be used to measure the effects of TLR9 on TLR4 signaling.

FIG. 6A-C. LPS signaling is attenuated by the TLR9 ligand CpG-DNA in enterocytes. (A) Comparison of phosphorylated p38 versus total p38 in a negative control, in the presence of 50 µg/ml LPS, in the presence of 50 µg/ml LPS and 10 µM CpG, and in the presence of 10 µM CpG. (B) Comparison of phosphorylated ERK versus total ERK in a negative control, in the presence of LPS, in the presence of LPS and CpG, and in the presence of CpG. (C) Bar graph showing the results of A.

FIG. 7A-E. LPS-mediated translocation in enterocytes which are either (A) untreated or treated with (B) 50 µg/ml LPS; (C) 50 µg/ml LPS+10 µM CpG; or (D) 10 µM CpG. (E) Bar graph showing the nuclear:cytoplasmic ratio for NF-κB in (A)-(D).

FIG. 8. CpG-DNA reduces LPS-mediated cytokine release from enterocytes. Bar graph showing the level of supernatant IL-6 in enterocytes which were either untreated ("CTRL") or treated with 50 µg/ml LPS, 50 m/ml LPS+10 µM CpG, or 10 µM CpG.

FIG. 9A-F. CpG-DNA reduces TLR4 signaling through TLR9 in enterocytes. (A) Western blot showing the amounts of TLR9 protein relative to actin in untreated enterocytes (Ctrl) or in enterocytes treated with 0.084 µM non-specific siRNA or siRNA specific for TLR9. (B)-(E) are immunofluorescence studies showing the relative amounts of p65 in the enterocyte nucleus versus its cytoplasm, when either (B) untreated or treated with (C) 50 µg/ml LPS; (D) 50 µg/ml LPS+10 µM CpG (in the context of normal TLR9 levels) or (E) 50 µg/ml LPS+10 µM CpG (in the context of TLR9 knockdown by siRNA). (E) Bar graph showing the results of (B)-(E).

FIG. 10. Experimental design to assess whether TLR9 activation affects TLR4-mediated inflammation in vivo.

FIG. 11A-B. Experiments according to the design shown in FIG. 10 showed that LPS-dependent signaling and inflammation were attenuated by CpG-DNA in the murine intestinal mucosa. (A). Western blot showing levels of signaling molecules phospho-p38 and phospho-ERK (relative to actin) in mice which were either untreated (Ctrl) or treated with LPS, LPS+CpG, or CpG. (B) Bar graph showing serum levels of the inflammatory cytokine IL-6 in mice which were either untreated (Ctrl) or treated with LPS, LPS+CpG, or CpG.

FIG. 12. TLR4 and TLR9 expression are unchanged by CpG-DNA and LPS in enterocytes. Western blot showing levels of TLR4 and TLR9 (relative to actin) in enterocytes which were either untreated (Ctrl) or treated with LPS, LPS+CpG, or CpG.

FIG. 13A-E. CpG-DNA causes a redistribution of TLR4 into internal structures in IEC-6 cells. Immunofluorescence studies showing TLR4 distribution in IEC-6 cells which were either untreated (A) or treated with (B) LPS; (C) LPS+CpG; or (D) CpG. (E) is a schematic drawing showing redistribution of TLR4 caused by TLR9.

FIG. 14A-D. LPS causes the internalization of TLR9, which is reversed by CpG-DNA. Immunofluoresence studies of IEC-6 cells showing TLR9 distribution in cells which were either (A) untreated; or treated with (B) LPS; (C) LPS+CpG; or (D) CpG.

FIG. 15. Schematic drawing showing development of a model system for necrotizing enterocolitis in the mouse.

FIG. 16. Western blot showing expression of TLR4 and TLR9 in control mice and mice modeling necrotizing enterocolitis ("NEC"), where the mice were produced according to the protocol diagramed in FIG. 15.

FIG. 17A-D. Gross and histologic anatomies of intestines, stressed by hypoxia, of normal versus TLR4 mutant mice. (A) Intestine of a TLR4 wildtype mouse, stressed by hypoxia, modeling necrotizing enterocolitis; (B) Intestine of a TLR4 mutant mouse, stressed by hypoxia; (C) histologic section from an intestine as depicted in (A); and (D) histologic section from an intestine as depicted in (B).

FIG. 18A-D. Histology of intestines from mice that were (A) breast fed (control); (B) gavage fed+hypoxic to model necrotizing enterocolitis (NEC); (C) breast fed and treated with 500 µg/kg (approximately 10 µg/animal, intraperitoneally injected) CpG (control); (D) gavage fed+hypoxic to model NEC and treated with 500 µg/kg (approximately 10 µg/animal, intraperitoneally injected) CpG.

FIG. 19A-H. (A-C) Immunohistochemical staining from murine terminal ileum showing actin bordering villi (indicated by large arrowheads) and caspase 3 (demonstrating apoptosis, indicated by small arrowheads) in a murine model of endotoxemia. (A) Control mice (injected with saline). (B) Mice injected with 5 mg/kg of LPS. (C) Mice injected with 5 mg/kg of LPS and 1 mg/kg of CpG. (D-G) Immunohistochemical staining of terminal ileum from newborn mice that were either breast fed ("control") or induced to develop NEC ("NEC"). Sections were stained for caspase 3 as a marker of apoptosis and enterocyte loss; positive staining is indicated by a small arrowhead. (D) Control injected with saline. (E) NEC injected with saline. (F) Control injected with 1 mg/kg CpG-DNA daily for four days. (G) NEC injected with 1 mg/kg CpG-DNA daily for four days. (H) Bar graph summarizing results, showing percent apoptosis in terminal ileum as depicted in (D)-(G).

FIG. 20A-I. Newborn mice were either breast fed ("control") or were induced to develop NEC ("NEC"). (A) Gross micrograph of intestine of a control mouse. (B) Gross micrograph of intestine of a control mouse treated with 1 mg/kg CpG-DNA daily for four days. (C) Gross micrograph of intestine of a NEC mouse. (D) Gross micrograph of intestine of a NEC mouse treated with 1 mg/kg CpG-DNA daily for four days. (E) Micrograph of histological section of intestine of a control mouse. (F) Micrograph of histological section of intestine of a control mouse treated with CpG. (G) Micrograph of histological section of intestine of a NEC mouse. (H) Micrograph of histological section of intestine of a NEC mouse treated with CpG. (I) Summary bar graph of the above results.

Figure 21:
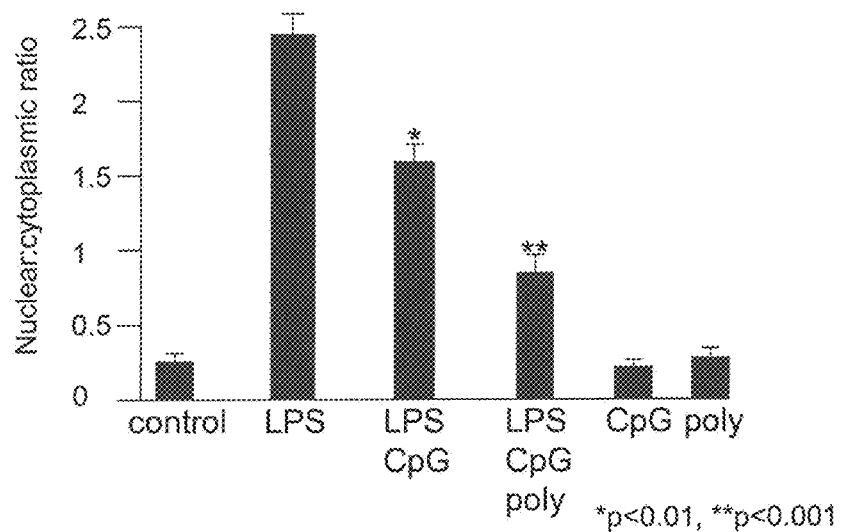

FIG. 21. Nuclear:cytoplasmic ratio of NFκB, indicating the extent of translocation of NFκB into the nucleus, in IEC-6 cells which were either untreated (control); treated with LPS; treated with LPS and CpG; treated with LPS, CpG and polymixin B; treated with CpG; or treated with polymixin B. The concentrations used were LPS at 50 CpG-DNA at 1 µM, and polymixin B at 10 µg/ml.

FIG. 22A-I. NOD2 expression is reduced in human and experimental NEC. A-D: Experimental NEC was induced in newborn mice using a combination of formula gavage and hypoxia while control mice remained breast fed by their mothers. A. Gross appearance of terminal ileum from breast fed mice. B: Histological appearance of the terminal ileum from breast fed mice. C. Gross appearance of the terminal ileum from mice with experimental NEC. D. Histological appearance of the terminal ileum from mice with experimental NEC. E. Gross and appearance of NEC in a preterm infant at the time of surgery. F. Microscopic appearance of NEC in a preterm infant at the time of surgery. G: Measurement of serum IL-6 in animals with NEC compared with control animals. H. Severity of NEC induced in wild-type and TLR-mutant animals demonstrating reduction in NEC in TLR4-mutant mice. I. Real-time PCR showing the expression of NOD2 in the intestine of mice (upper blot) and infants (lower blot) with NEC as compared with controls without NEC. Representative of 6 separate experiments. *p<0.05 vs. control by ANOVA.

FIG. 23A-E. MDP prevents TLR4-mediated NFkB translocation in IEC-6 enterocytes. A. Confocal microscopic image demonstrating the immunolocalization of NFkB (p65 subunit) in untreated IEC-6 cells, revealing a cytoplasmic appearance; B. LPS treatment causes a nuclear distribution of NFkB, indicating that nuclear translocation has occurred; C. Pre-treatment of IEC-6 cells with MDP maintains a cytoplasmic appearance of NFkB, indicating that MDP limits TLR4-mediated NFkB translocation; D. Cytoplasmic appearance of NFkB in IEC-6 cells treated with MDP alone, indicating that MDP has minimal stimulatory effects on NFkB translocation in IEC-6 cells; E. Quantification of NFkB translocation in IEC-6 cells in the conditions indicated. Representative of 5 separate experiments. **p<0.05 vs. control by ANOVA, *p<0.05 vs. LPS by ANOVA.

FIG. 24A-C. MDP inhibits TLR4 signaling in enterocytes. A. IL-6 release in vitro as determined by ELISA in IEC-6 cells that were either untreated, or treated with LPS in the presence or absence of MDP. B. Serum IL-6 release in vivo in wild-type (open bars) and NOD2-deficient mice (solid bars) that were either pre-treated with saline or MDP then injected with LPS. C. SDS-PAGE showing the expression of phosphorylated ERK and beta-actin in IEC-6 cells that were treated with media (control), LPS, LPS with MDP, LPS with MDP-C which is a non-stimulatory analogue of MDP, and either MDP or MDP-C alone. **p<0.05 vs. control by ANOVA, *p<0.05 vs. LPS by ANOVA.

FIG. 25. MDP treatment decreases TLR4 expression in enterocytes. Newborn mice were treated with LPS after pre-treatment with either saline or MDP. Three hours later mucosal scrapings were harvested from the terminal ileum, and subjected to RT-PCR for expression of TLR4. Representative of 4 separate experiments. Duplicate samples are shown for each group.

FIG. 26A-E. MDP prevents against the development of experimental NEC in vivo in newborn mice. Newborn mice were injected with saline or MDP daily for four days, and then were induced to develop NEC. A. Histology (H&E) of terminal ileum of breast fed mouse treated with saline control. B. Histology (H&E) of terminal ileum of breast fed mouse treated with MDP. C. Histology (H&E) of terminal ileum of mouse pre-treated with saline, after which NEC was induced. D. Histology (H&E) of terminal ileum of mouse pre-treated with MDP, after which conditions which induced NEC in saline-treated mice were applied. E: Severity of NEC in newborn mice as scored by a blinded pediatric pathologist. *p<0.05 vs. NEC in saline-injected mice. Representative of three separate experiments with over 5 animals per group.

FIG. 27A-G. CpG-ODN-HS and CpG-DNA reduce the development of experimental NEC in vivo in newborn mice. Newborn NEC and control mice were injected with CpG-ODN-HS or CpG-DNA. A. Histology (H&E) of terminal ileum of breast fed mouse. B. Histology (H&E) of terminal ileum of mouse after induction of NEC. C. Histology (H&E) of terminal ileum of mouse treated with CpG-DNA, after which conditions which induced NEC were applied. D. Histology (H&E) of terminal ileum of mouse treated with CpG-ODN-HS, after which conditions which induced NEC were applied. E. Histology (H&E) of terminal ileum of breast fed mouse treated with CpG-ODN-HS. F. Histology (H&E) of terminal ileum of breast fed mouse treated with CpG-DNA. G. Severity of NEC in newborn mice as scored by a blinded pediatric pathologist. *p<0.05 vs. NEC in saline-injected mice.

Figure 28:
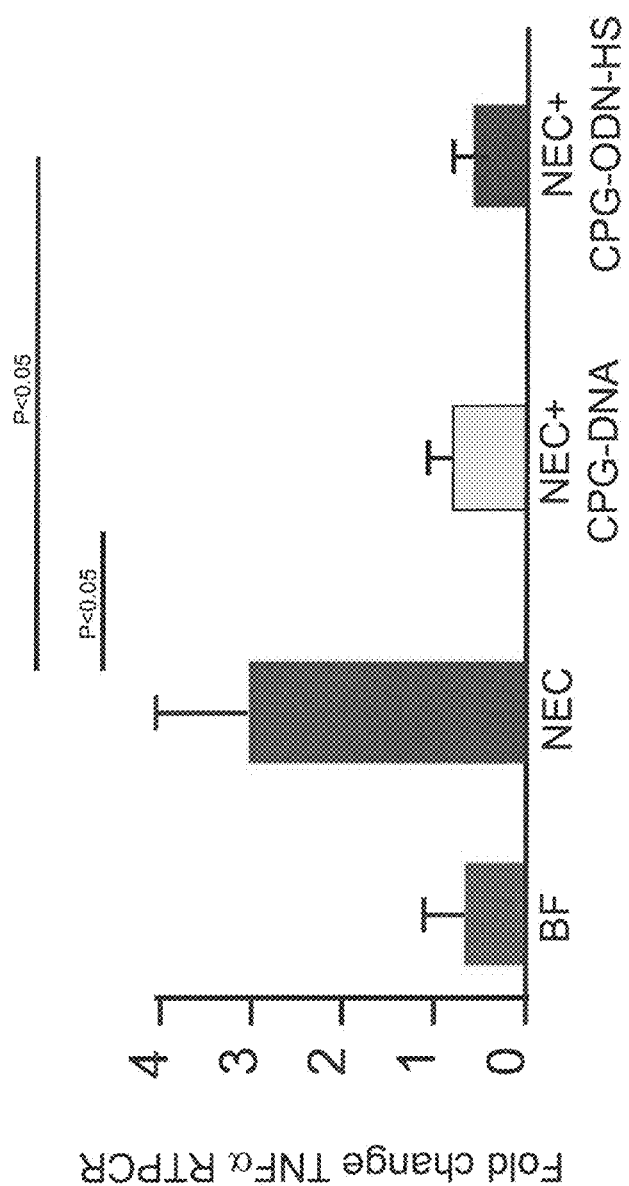
Figure 29:
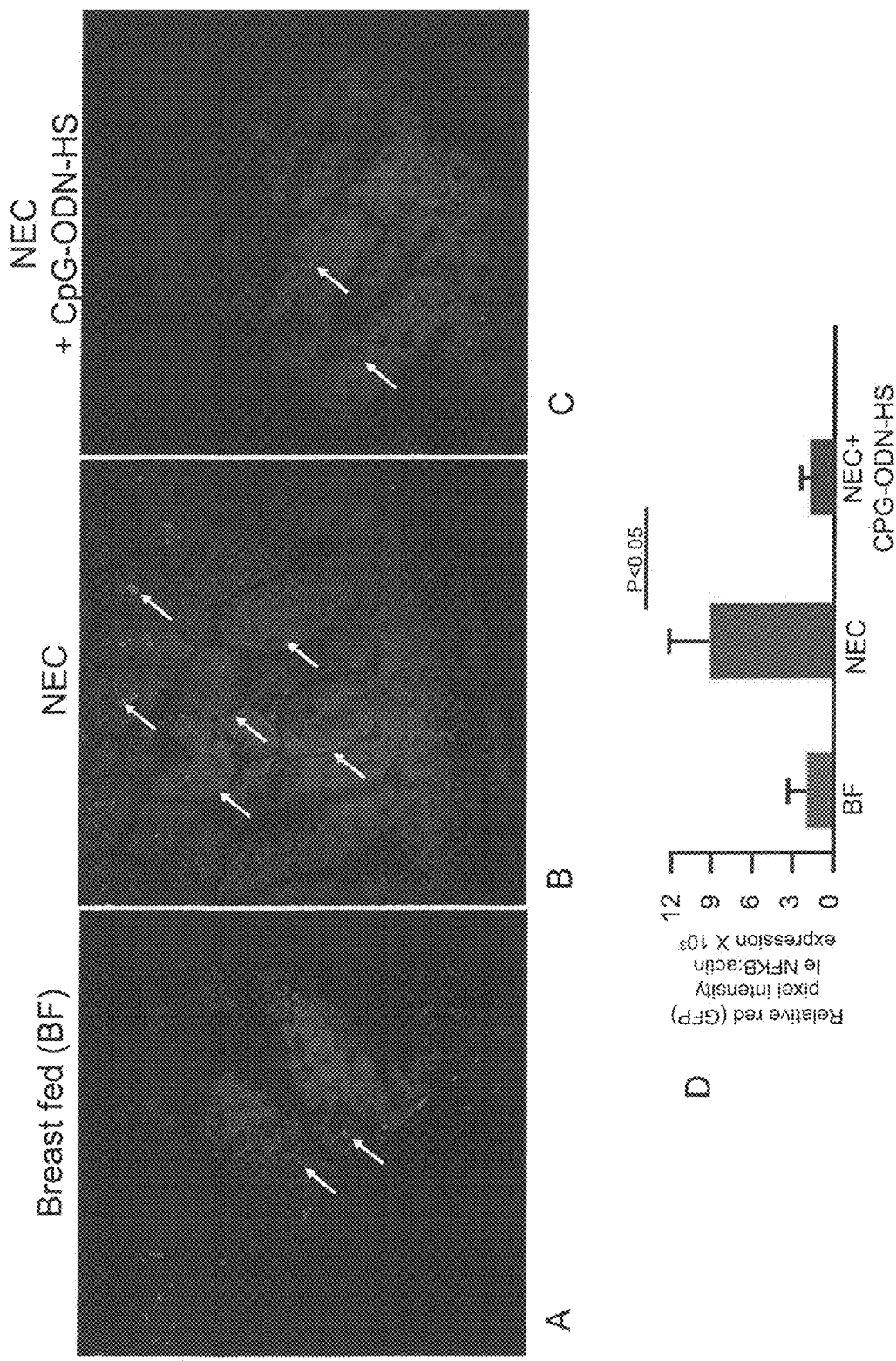

FIG. 28. CpG-ODN-HS and CpG-DNA reduce the expression of mucosal TNF-α in NEC newborn mice in vivo.

FIG. 29A-D. Confocal microscopy showing the extent of NFkB activation in mice with NEC in the absence or presence of CpG-ODN-HS. CpG-ODN-HS reduces the level of NFkB activation in NEC newborn mice in vivo. The mice express NFkB-GFP, and sections were stained with anti-GFP antibody (red; arrow).

Figure 30B:
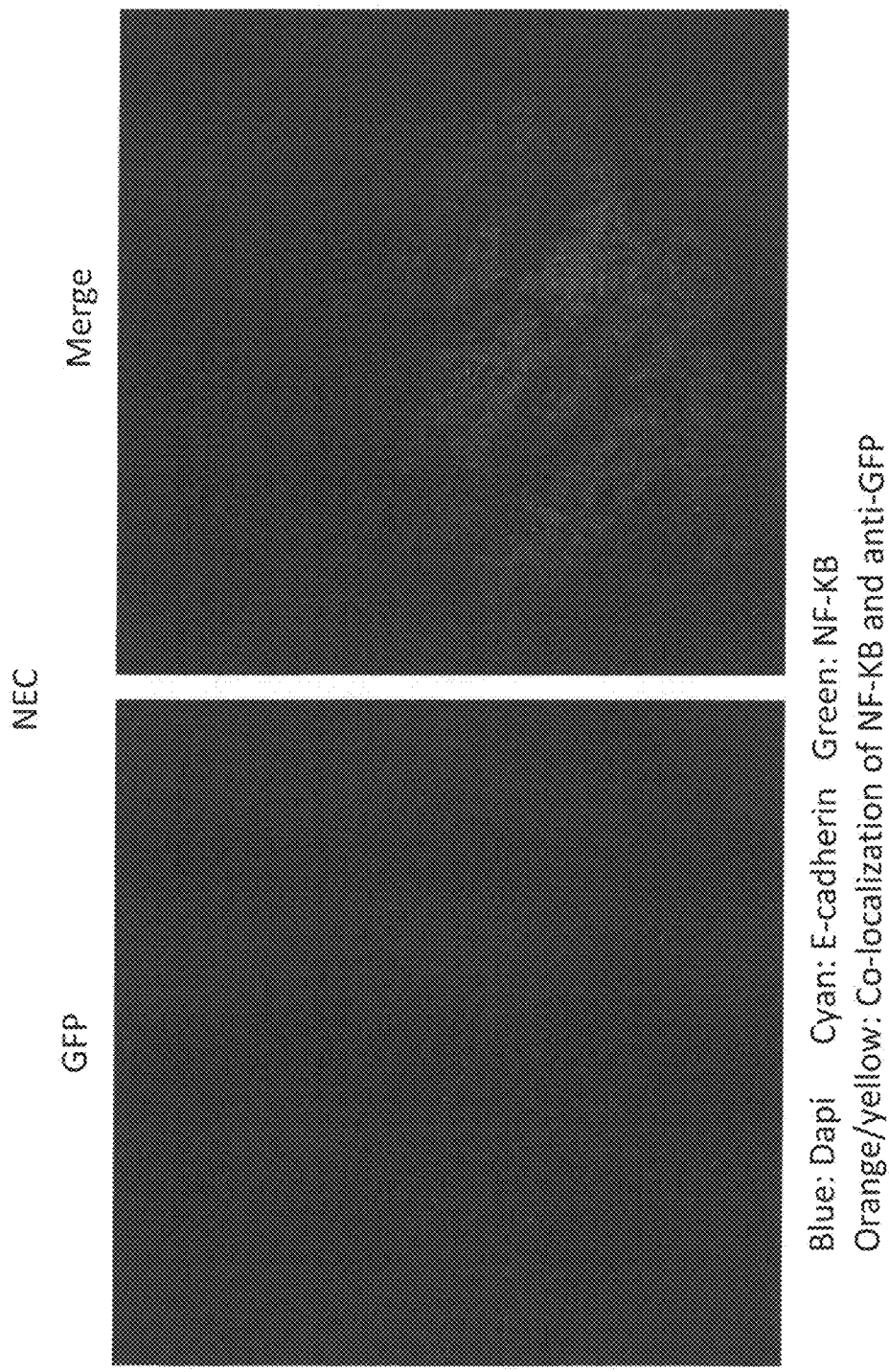
Figure 30C:
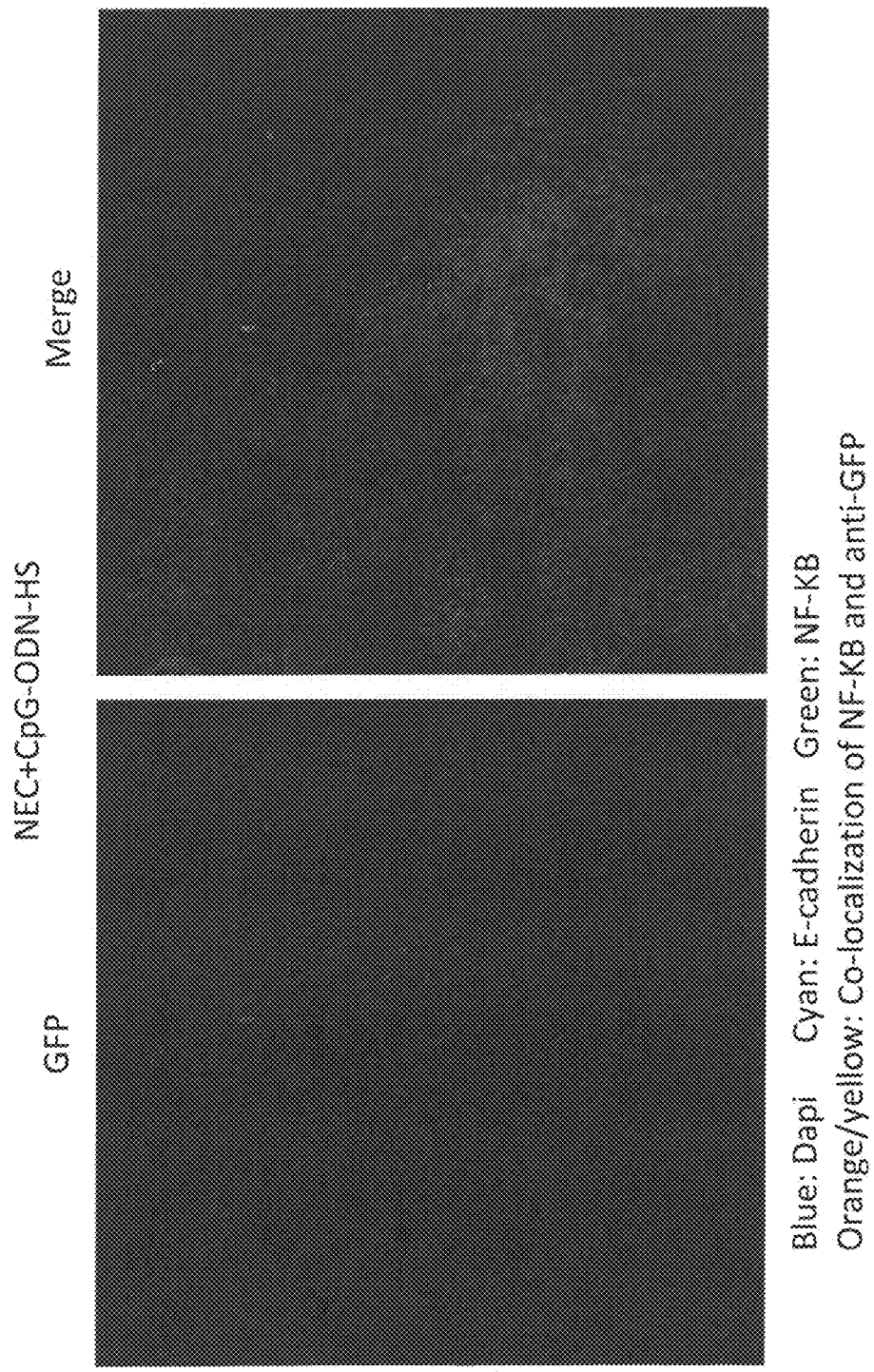

FIG. 30A-C. Confocal microscopy showing the colocalization of NFkB and E-cadherin in breast fed (A), NEC (B) and NEC mice treated with CpG-ODN-HS.

5. DETAILED DESCRIPTION OF THE INVENTION

For clarity of description, and not by way of limitation, the detailed description of the invention is divided into the following subsections:
(i) disorders associated with TLR4 activation;
(ii) TLR9 agonists;
(iii) NOD2 agonists;
(iv) TLR4 antagonists;
(v) methods of prevention;
(vi) methods of treatment; and
(vii) pharmaceutical/nutriceutical compositions.

5.1 Disorders Associated with TLR4 Activation

TLR4-associated disorders in which endotoxin has been implicated (also referred to as "endotoxin-related, TLR4-associated disorders") (Prohinar et al., 2007, J. Biol. Chem. 282:1010-1017) include NEC (Anand et al., 2007, Shock 27:124-133) and systemic sepsis (also "sepsis," "septic shock" or "endotoxemia"; Neal et al., 2006, J. Immunol. 176:3070-3079). Other disorders associated with TLR4 activation include, but are not limited to, non-typeable *Haemophilus influenza* infection (Shuto et al., 2001, Proc. Natl. Acad. Sci. U.S.A. 98(15):8774-8779), asthma (Shan et al., 2006, Am. J. Physiol. Lung Cell Mol. Physiol. 291: L324-L333), atherosclerosis (Yang et al., 2005, Biotechnol. 42(3): 225-236), and ischemic reperfusion injury (Zhai et al., 2004, J. Immunol. 173:7115-7119).

5.2 TLR9 Agonists

Agonists (activators) of TLR9 which may be used according to the invention include oligonucleotides comprising one or more unmethylated CpG dinucleotide ("CpG ODNs"). In non-limiting embodiments of the invention, such oligonucleotides may contain phosphorothioate linkages (at some or all bonds) or other modifications which improve stability, uptake, etc. A number of CpG ODNs that activate TLR9 are known in the art. Some are species specific.

Human CpG ODNs have been divided into three types, as follows:
  Type A (D) CpG ODNs, which have polyG motifs with phosphohorothioate linkages at the 5' and 3' ends and a PO-containing palindrome CpG-containing motif at its center—these are strong inducers of IFN-alpha production by plasmacytoid dendritic cells and are potent NK cell activators;
  Type B (K) CpG ODNs, which have a full phosphorothioate backbone with one or more CpG motifs without polyG; they are potent activators of B cells but weaker inducers of IFN-alpha production; and
  Type C CpG ODNs, which have a complete phosphorothioate backbone without polyG, but have CpG motifs and palindromes; they produce A and B-like effects (stimulate IFN-alpha and B cells).

Either type A, type B or type C human-selective CpG ODNs may be used according to the invention, although type B CpG ODNs are preferred. Non-limiting example of CpG ODNs which are selectively active in humans and may be used according to the invention include, but are not limited to, 5'-TCG TCG TTT TGT CGT TTT GTC GTT-3' (SEQ ID NO:1; CpG ODN 2006, InvivoGen, San Diego, Calif.), CpG ODN 2006-G5 (InvivoGen, San Diego, Calif.), 5'-GGG GGA CGA TCG TCG GGG GG-3' (SEQ ID NO:2; CpG ODN 2216, InvivoGen, San Diego, Calif.), 5'-TCG TCG TCG TTC GAA CGA CGT TGA T (SEQ ID NO:3; CpG ODN M362, InvivoGen, San Diego, Calif.), 5'-TCG TCG TTT TGT CGT TTT GTC GTT-3' (SEQ ID NO:4; CpG ODN 7909, Coley Pharmaceutical Group, Ottawa, Ontario, Canada), D(5'-TCT-GTCGTTCT-X-TCTTGCTGTCT-5) (SEQ ID NO:5) where X is a glycerol linker (Idera Pharmaceuticals, Cambridge, Mass.; see Putta et al., Nucl. Acids Res. 34(11):3231-3238), TCCATGACGTTCCTGACGTT (SEQ ID NO:6; ODN 1826, preferably phosphorothioated), d(5'-TCTGTC*GTTCT-X-TCTTGC*TGTCT-5') (SEQ ID NO:7) where C*=N³-Me-dC and X is a glycerol linker (Idera Pharmaceuticals, Cambridge, Mass.; see Putta et al., Nucl. Acids Res. 34(11):3231-3238), and d(5'-TCTGTCG*TTCT-X-TCTTG*CTGTCT-') (SEQ ID NO:8) where G*=N¹-Me-dG and X is a glycerol linker (Idera Pharmaceuticals, Cambridge, Mass.; see Putta et al., Nucl. Acids Res. 34(11):3231-3238).

In further embodiments, the present invention provides for the use of CpG ODNs which are at least 90 percent and preferably at least 95 percent homologous to any of the CpG ODNs referred to herein (where homology may be determined by standard software such as BLAST or FASTA).

In one particular, non-limiting embodiment, the CpG ODN, 5'-TCCATGACGTTCCTGACGTT-3' (SEQ ID NO:6), containing phosphorothioate linkages, known in the art as CpG ODN 1826 (Coley Pharmaceutical Group, Ottawa, Ontario, Canada), which shows selective activation of murine TLR9, may be used. In addition, CpG ODNs which are at least about 90 percent, and preferably at least about 95 percent, homologous to CpG ODN 1826 may be used, where homology may be measured using a standard software program such as BLAST or FASTA.

In yet another specific, non-limiting embodiment, the CpG-ODN 5' TCGTCGTTTTGTCGTTCCTGACGTT 3' (SEQ ID NO:10), referred to herein as CpG-ODN-HS, may be used. In addition, CpG ODNs which are at least about 90 percent, and preferably at least about 95 percent, homologous to CpG ODN HS may be used, where homology may be measured using a standard software program such as BLAST or FASTA. In non-limiting embodiments of the invention, a mixture of two or more CpG ODNs may be used.

In some non-limiting embodiments, the CpG ODN is at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 nucleotides in length.

In some non-limiting embodiments, the CpG-ODN is up to about 25, up to about 30, up to about 35, up to about 40, up to about 45 or up to about 50 nucleotides in length.

The CpG-ODN may optionally be linked to a carrier compound which may or may not be a nucleic acid, for example, but not limited to, a transport peptide that facilitates cellular uptake. The CpG-ODN may optionally be complexed with one or more additional compound, such as a peptide, or comprised in a micelle or liposome, to facilitate uptake.

In one non-limiting embodiment, the CpG ODN is about 15, about 16, about 17, about 18, about 19, about 20, about 21, about 22, about 23, about 24, about 25, about 26, about 27, about 28, about 29, about 30, about 31, about 32, about 33, about 34, or about 35 nucleotides in length.

In some non-limiting embodiments, the CpG-ODN comprises the sequence 5' GTCGTT 3'.

In some non-limiting embodiments, the CpG-ODN comprises the sequence 5' GTCGTTT 3'.

In some non-limiting embodiments, the CpG-ODN comprises the sequence 5' CGTCGTTT 3'.

In some non-limiting embodiments, the CpG-ODN comprises the sequence 5' GTCGTTTT 3'.

In some non-limiting embodiments, the CpG-ODN comprises the sequence 5' CGTCGTTTT 3'.

In some non-limiting embodiments, the CpG-ODN comprises the sequence 5' GTCGTTTTGTC 3'.

In some non-limiting embodiments, the CpG-ODN comprises the sequence 5' TCGTCGTTTTGTC 3'.

In some non-limiting embodiments, the CpG-ODN comprises the sequence 5' GACGTT 3'.

In some non-limiting embodiments, the CpG-ODN comprises the sequence 5' TGACGTT 3'.

In some non-limiting embodiments, the CpG-ODN comprises the sequence 5' CTGACGTT 3'.

In some non-limiting embodiments, the CpG-ODN comprises the sequence 5' TCCTGACGTT 3'.

In some non-limiting embodiments, the CpG-ODN comprises one or more of 5' GTCGTTTTGTC 3', for example, one, two, three or four of 5' GTCGTTTTGTC 3'.

In some non-limiting embodiments, the CpG-ODN comprises one or more copy of 5' GTCGTT 3', 5' GTCGTTT 3', 5' CGTCGTTT 3', 5' GTCGTTTT 3', 5' CGTCGTTTT 3' SEQ ID NO:16, SEQ ID NO:17, or a combination thereof, for example, one, two, three or four copy or copies of 5' GTCGTT 3', 5' GTCGTTT 3', 5' CGTCGTTT 3', 5' GTCGTTTT 3', 5' CGTCGTTTT 3' SEQ ID NO:16, SEQ ID NO:17, or a combination thereof.

In some non-limiting embodiments, the CpG-ODN comprises one or more copy of 5' GTCGTT 3', for example, one, two, three or four copy or copies of 5' GTCGTT 3', and also comprises one or more copy or copies of 5' GACGTT 3', 5' TGACGTT 3', 5' CTGACGTT 3', SEQ ID NO: 21, or a combination thereof.

In some non-limiting embodiments, the CpG-ODN comprises one or more copy of 5' GTCGTT 3', 5' GTCGTTT 3', 5' CGTCGTTT 3', 5' GTCGTTTT 3', 5' CGTCGTTTT 3' SEQ ID NO:16, SEQ ID NO:17, or a combination thereof, for example, one, two, three or four copy or copies of SEQ ID NO:11, and also comprises one or more copy or copies of 5' GACGTT 3', 5' TGACGTT 3', 5' CTGACGTT 3', SEQ ID NO:21, or a combination thereof. In some nonlimiting embodiments, the CpG-ODN comprises 5' GTCGTT 3' and 5' GACGTT 3'.

For additional TLR9 agonists, see Daubenberger, 2007, Curr. Opin. Molec. Ther. 9:45-52 and Krieg, 2006, Nat. Rev. Drug Disc. 5:471-484.

In non-limiting embodiments, the present invention provides for methods of identifying TLR9 agonists which may be used according to the invention comprising identifying a molecule which is capable of binding to TLR9 under physiologic conditions and which, in an in vivo system, in the presence of a TLR4-activating amount of LPS, decreases one or more of the relative amount of phosphorylated p38, the relative amount of phosphorylated ERK, the relative translocation of NF-κB into the nucleus, or the amount of IL-6 produced. In addition to identifying test agents suitable for TLR9 activation, such method may also be used to confirm the activity or optimize the dosage of any of the particular CpG ODNs listed herein.

5.3 NOD2 Agonists

Any agonist (activator) of NOD2 may be used according to the invention. In specific non-limiting embodiments of the invention, the activator of NOD2 is muramyl-di-peptide ("MDP"). MDP may be obtained, for example but not by way of limitation, from InvivoGen (San Diego, Calif.). Alternatively, a molecule comprising MurNAc attached to L-ALa and D-isoGln other than MDP may be used. Additional non-limiting examples of NOD2 agonists include, but are not limited to, MurNAc-L-Ala-D-isoGln, also called GM-Di; MurNAc-L-Ala-γ-D-Glu-L-Lys, also called MtriLYS; and iDAP.

5.4 TLR4 Antagonists A number of inhibitors/antagonists of TLR4 which may be used according to the invention (in a subset of embodiments) include, but are not limited to, LPS antagonists, for example, the following:

LPS from *E. coli* K12 msbB (InvivoGen, San Diego, Calif.);

polymyxin B (polymixin B; polymyxin B sulfate);

CyP (Macagno et al., 2006, J. Exp. Med. 203(6):1481-1492);

lipid IVa;

E5531 (Kobasyashi et al., 1998, Antimic. Ag. Chemother. 42(11):2824-2829); and

E5564 (eritoran, Eisai Co., Tokyo, Japan; Mullarkey et al., 2003, J. Pharm. Exp. Ther. 304(3): 1093-10102; Rossignol et al., 2004, Antimicrob. Agents Chemother. 48(9):3233-3240).

In a further non-limiting embodiment of the invention, an antibody (including conventional immunoglobulin, single-chain antibody, a Fab fragment, a Fv fragment, a single-chain Fv fragment, etc.) that antagonizes TLR4 activity may be used. Such an antibody may be prepared using standard techniques. The ability of such an antibody to act as an antagonist of TLR4 may be confirmed by the ability of the antibody to block a LPS induced index of TLR4 activation, such as an increase in relative phosphorylation of p38 or ERK or an increase in IL-6.

5.5 Methods of Prevention

In specific, non-limiting embodiments, the present invention provides for methods of preventing NEC in an infant (for example, a premature infant or a term infant otherwise at risk for the disease) comprising administering, to the infant, an effective amount of an agonist of NOD2, such as but not limited to muramyl-di-peptide, which reduces the risk of the infant developing NEC.

According to the invention, "methods of preventing" are defined as methods which reduce the risk of developing the disease, and do not necessarily result in 100% prevention of the disease. As such, these methods, applied prophylactically to an infant, may not only reduce the risk but may also reduce the severity of the disease if it does occur. By definition, such preventative methods may be administered to an infant having no signs of preexisting NEC as well as to an infant which is exhibiting one or more early clinical sign consistent with NEC but in which a definitive diagnosis of NEC has not been established.

The NOD2 agonist may be administered by any route known in the art, including oral administration, intravenous administration, and administration directly into the intestine.

In specific, nonlimiting embodiments, the NOD2 agonist may be administered at a dose of between about 0.1 and 10 mg/kg, or between 0.5 mg/kg and 5 mg/kg. In specific, non-limiting embodiments, the NOD2 agonist may be MDP administered at a dose of between about 0.1 and 10 mg/kg, or between 0.5 mg/kg and 5 mg/kg, or about 1 mg/kg. The dose may be administered at least once a day for a period of between one day and ten days, or between one day and five days, or at least three days, or at least four days, or at least five days, or until the infant is determined to no longer be at risk for developing NEC.

Such methods may further comprise administering an effective amount of an agonist of TLR9 and/or an antagonist of TLR4. In such methods, the TLR9 agonist and/or TLR4 antagonist may be administered together with the NOD2 agonist or separately.

5.6 Methods of Treatment

In a first set of embodiments, the present invention provides for a method of treating a TLR4-associated disorder in a subject comprising administering, to the subject, an effective amount of a TLR9 agonist. In a subset of such embodiments, the present invention provides for further administering, to the subject, an effective amount of a TLR4 antagonist.

In a related, second set of embodiments, the present invention provides for a method of treating an endotoxin-related, TLR4-associated disorder in a subject comprising administering, to the subject, an effective amount of a TLR9 agonist. In a subset of such embodiments, the present invention provides for further administering, to the subject, an effective amount of a TLR4 antagonist.

When a TLR9 agonist and a TLR4 antagonist are administered in the same regimen, the effective amounts of TLR9 and TLR4 may be such that the net effect is a decrease in indices of inflammation, whereas the amounts of each agent if used individually may be either effective or ineffective (in other words, the effective dose when the agents are used in combination may be lower than the effective doses of each agent used individually, although individually effective doses of each agent may also be used in combination). Accordingly, the present invention provides for a method of treating a TLR4-associated disorder, comprising administering, to a subject in need of such treatment, an effective amount of a TLR9 agonist and a TLR4 antagonist.

The TLR9 agonist and/or TLR4 antagonist may be administered by any route known in the art, including, but not limited to, intravenous, intraarterial, oral or rectal (including via an orally or rectally inserted catheter) administration. Where both TLR9 agonist and TLR4 antagonist are included in a treatment regimen, they may be administered concurrently or in series.

An effective amount of a TLR9 agonist is an amount which can suppress the effect of LPS in an in vitro or in vivo system, preferably reducing a marker of inflammation, such as relative phospho-p38 expression NF-κB translocation to the nucleus, or IL-6 production, by at least about 10 percent or at least about 20 percent. The amount may be a concentration or a dosage in an organism. For example, but not by way of limitation, the dose range at which a TLR9 activator, such as CpG ODN, may be administered may be between about 100 µg/kg and 10 mg/kg, or between about 100 µg/kg and 1 mg/kg, or about 500 µg/kg, which may be administered as a single dose or a divided dose.

An effective amount of a TLR4 antagonist is an amount which can suppress the effect of LPS in an in vitro or in vivo system, preferably reducing a marker of inflammation, such as relative phospho-p38 expression NF-κB translocation to the nucleus, or IL-6 production, by at least about 5 percent, at least about 10 percent or at least about 20 percent, or more when used together with a TLR9 agonist. The dose range at which TLR4 inhibitors may be administered may be, for example but not by way of limitation, as follows (in single or divided doses):

for LPS from *E. coli* K12 msbB (InvivoGen, San Diego, Calif.) between about 100 µg/kg and 1 mg/kg;

for polymyxin B between about 1-5 mg/kg and preferably between 2-3 mg/kg;

for CyP between about 30 mg/kg and 50 mg/kg;

for lipid IVa between about 100 µg/kg and 1 mg/kg;

for E5531 between about 10 µg/kg and 1 mg/kg; and for E5564, for a human subject, between about 20 mg and 200 mg, or between about 40 mg and 110 mg, said dose administered in divided doses over a period of time ranging from about 2 to 7 days, preferably between about 80 and 120 mg or about 105 mg administered over a 6 day period (e.g., 11 doses administered at 12 hour intervals) (http://www.japan-corp.net/Article.Asp?Art_ID=10765).

In further specific, non-limiting embodiments, the present invention provides for methods of reducing the severity of NEC in an infant suffering from the disease, comprising administering to the infant an effective amount of an agonist of NOD2, such as but not limited to muramyl-di-peptide. In specific, nonlimiting embodiments, the NOD2 agonist may be administered at a dose of between about 0.1 and 10 mg/kg, or between 0.5 mg/kg and 5 mg/kg. In specific, non-limiting embodiments, the NOD2 agonist may be MDP administered at a dose of between about 0.1 and 10 mg/kg, or between 0.5 mg/kg and 5 mg/kg, or about 1 mg/kg. The dose may be administered at least once a day for a period of between one day and ten days, or between one day and five days, or at least three days, or at least four days, or at least five days, or until the infant is determined to no longer be at risk for developing NEC. Such methods may further comprise administering an effective amount of an agonist of TLR9 and/or an antagonist of TLR4 (as set forth above).

The methods of treatment according to the invention may further comprise the use of other biologically active agents, for example agents which had hitherto been used in the art to treat the TLR4 associated disorder, but where the addition of the inventive method and/or composition provides substantial therapeutic benefit. For example, but not by way of limitation, the treatment of NEC or sepsis may further include the administration of one or more antibiotic agent.

"Treatment" according to the invention includes, without limitation, (1) decreasing the level of one or more index of inflammation (e.g., inflammatory cytokines such as TNF-α, IL-6, IL-12p40, IL-1β; (2) decreasing a clinical marker of inflammation, such as leukocyte count, fever, hypotension; and/or (3) reducing the risk of an adverse outcome, such as death, organ failure, hypoxia, or the need for surgery. "Treatment" does not necessarily mean that the condition being treated will be cured.

5.7 Pharmaceutical/Nutraceutical Compositions

The present invention, in non-limiting embodiments, provides for therapeutic compositions.

In one set of embodiments, the therapeutic composition is a kit comprising, in separate containers, a pharmaceutical composition comprising an effective amount of a TLR9 agonist and a pharmaceutical composition comprising an effective amount of a TLR4 antagonist.

In another set of embodiments, the therapeutic composition is a pharmaceutical composition comprising an effective amount of a TLR9 agonist and a TLR4 antagonist in a suitable pharmaceutical carrier.

In yet another set of embodiments, the present invention provides for a pharmaceutical composition comprising an effective concentration of NOD2 agonist which may optionally further comprise an effective concentration of one or more TLR9 agonist and/or an effective concentration of one or more TLR4 antagonist.

An effective amount or an effective concentration of a TLR9 agonist, a NOD2 agonist, or a TLR4 antagonist is a concentration which, when administered in a volume suitable to the chosen route of administration, results in an effective dosage as set forth above.

In a non-limiting embodiment, the present invention provides for an infant formula (e.g., nutritional formulation) which comprises an effective amount of an agonist of NOD2, optionally further comprising an effective amount of an agonist of TLR9 and/or an effective amount of an antagonist of TLR4. When administered in the amount recommended for nutritional purposes, an effective dosage of NOD2 agonist and optionally TLR9 agonist and/or TLR4 inhibitor may be administered. In a specific, non-limiting example, the NOD2 agonist is MDP.

6. EXAMPLE 1

Both TLR4 and TLR9 were demonstrated on the surface of enterocytes from mice and humans. FIG. 1 and FIG. 2A show Western blots depicting expression of TLR4 and TLR9 in positive control cells and enterocytes from C57/B16. FIG. 2B shows an image from an immunofluorescence study demonstrating expression of TLR4 and TLR9 in murine intestine. FIG. 3 shows the results of a comparable immunofluorescence study performed using intestine from human neonates.

Experiments were performed to validate a model for the etiology of NEC, where, in the context of physiologic stressors such as hypoxia, infection, and/or prematurity, bacterial DNA and endotoxin from lumenal bacteria can activate TLR4 as well as suppressor pathways involving TLR9 (FIG. 4). A variety of molecules may be used to measure the activation level of TLR4, including MAP kinases such as p38 and ERK and NFκB or its subunits, p65 or p50 (FIG. 5).

A first series of experiments was designed to study the consequences of the TLR4 activator LPS and a CpG TLR9 agonist on the mediators of activated TLR4, p38 and ERK. Throughout this example section, the CpG used was CpG ODN, 5'-TCCATGACGTTCCTGACGTT-3' (SEQ ID NO:6) P38 and ERK are both phosphorylated in their activated form. As shown in FIG. 6A-C, the relative levels of phosphorylated p38 and ERK increased when enterocytes were exposed to LPS. However, when enterocytes were exposed to both LPS and CpG, the magnitude of this increase was significantly less (see especially FIG. 6C). These studies show that LPS signaling is attenuated by the TLR9 ligand CpG-DNA in enterocytes.

A second series of experiments was designed to study the consequences of the TLR4 activator LPS and the TLR9 activator CpG on the mediator of activated TLR4, NFκB. As shown by comparing FIGS. 7A and B, LPS causes NFκB to translocate into the nucleus. The extent of translocation caused by LPS is decreased by co-exposure to CpG (FIGS. 7C and E). Accordingly, these studies show that LPS-mediated NF-κB translocation in enterocytes is attenuated by the TLR9 agonist CpG.

A third series of experiments, depicted in FIG. 8, showed that, in studies similar to those described above, CpG-DNA reduces LPS-mediated cytokine release from enterocytes.

All the foregoing three series of experiments have shown that CpG (an activator of TLR9) inhibited the effects of TLR4 activation, including its role in promoting inflammation. To test whether CpG was, in fact, acting through TLR9, "knockdown" studies were performed in which TLR9-specific interfering RNA (siRNA) was used to reduce expression of TLR9 (see Western blot of FIG. 9A, which shows that the level of TLR9 protein was effectively suppressed). As shown in FIGS. 9E and F (relative to FIGS. 9C and D), the attenuating effect of CpG on translocation of NFκB subunit p65 was virtually eliminated in enterocytes in which TLR9 expression was suppressed by siRNA. These studies indicate that, in enterocytes, CpG-DNA reduces TLR4 signaling through TLR9.

Further experiments were performed to study the mechanism by which TLR9 suppresses the TLR4 activation. Surprisingly, as shown in FIG. 12, TLR4 and TLR9 expression are unchanged by CpG-DNA and LPS in enterocytes. Rather, as shown in FIG. 13A-E, it appears that CpG-DNA causes a redistribution of TLR4 into internal enterocyte structures. In particular, the experiments showed that while LPS causes the internalization of TLR9, this effect is reversed by CpG-DNA (FIG. 14A-D).

Experiments were then designed to determine whether the above phenomena, observed in vitro, could be confirmed in vivo (see FIG. 10). As shown in FIG. 11A-B, experiments according to the design shown in FIG. 10 showed that LPS-dependent signaling and inflammation, as measured by levels of phosphorylated p38 and ERK and by serum IL-6 levels, were attenuated by CpG-DNA in the murine intestinal mucosa.

To determine the relevance of all the above observations to NEC, a murine model of NEC was developed, in which hypoxia was used to induce a pathology comparable to NEC in newborn mice (FIG. 15). FIG. 16 presents a Western blot showing expression of TLR4 and TLR9 in control mice and mice modeling necrotizing enterocolitis ("NEC"). A substantial increase in the level of TLR4, and a decrease in TLR9, was observed. Interesting, the NEC-like pathology could not be induced in mice carrying a TLR4 mutation (FIG. 17A-D).

Finally, CpG was found to limit the severity of experimental NEC induced in wild-type TLR4 animals (FIG. 18A-D).

7. EXAMPLE 2

Materials and Methods

Cell culture and reagents. IEC-enterocytes and J774 macrophages were obtained from the American Type Culture Collection (ATCC, Manassas, Va.). Phosphorothioated CpG-DNA, oligodeoxynucleotide (ODN) 1826 (TCCATGACGT-TCCTGACGTT) (SEQ ID NO:6), and control GpC-DNA, control ODN 1826 (TCCATGAGCTTCCTGAGCTT) (SEQ ID NO:9), were synthesized by the University of Pittsburgh DNA synthesis facility. ODNs were confirmed to be endotoxin-free by Limulus assay. Antibodies were obtained as follows: TLR4; TLR9-Imgenex, San Diego, Calif.; NFkB (p65 subunit)— Santa Cruz Biotechnology, Santa Cruz, Calif.; cleaved caspase-3, phospho-p38-MAPK, phospho-ERK, total p38-MAPK, and total ERK—Cell Signaling Technology, Beverly, Mass.

Induction of necrotizing enterocolitis. All mice were housed and cared for at Rangos Research Center, Children's Hospital of Pittsburgh. All experiments were approved by the Children's Hospital of Pittsburgh Animal Care Committee and the Institutional Review Board of the University of Pittsburgh (protocol 45-06). Swiss-Webster (CfW) and C57/B1-6 mice were obtained from Jackson Laboratories (Jackson Laboratory, Bar Harbor, Me.). Endotoxemia was induced in 2 week old C57/B16 or CpG1 (TLR9-mutant) mice by the intraperitoneal injection of LPS (*Escherichia coli* 0111:B4 purified by gel-filtration chromatography, >99% pure, 5 mg/kg, Sigma-Aldrich, St. Louis, Mo.). In parallel, mice were administered vehicle (saline) or CpG-DNA (1 mg/kg). Three hours after injection, animals were sacrificed. To induce experimental NEC, 10-14 day-old mice (Swiss-webster, C57B1-6 or TLR9-mutant (CpG1)) were gavage fed (Similac Advanced infant formula (Ross Pediatrics): Esbilac canine milk replacer at a ratio of 2:1) five times daily, and exposed to intermittent hypoxia (5% $O_2$, 95% $N_2$) for 10 minutes using a modular hypoxic chamber (Billups-Rothenberg, DelMar, Calif.) twice daily for 4 days. Animals were fed 200 microliters per 5 grams of mouse body weight by gavage over 2-3 minutes, using a 24-French angio-catheter which was placed into the mouse esophagus under direct vision. Samples were harvested at day four for analysis. It has been demonstrated that this experimental protocol induces intestinal inflammation and the release of pro-inflammatory cytokines in a pattern that closely resembles human NEC. Control (i.e. non NEC) animals remained with their mothers and received breast milk. Where indicated, breast fed animals of all strains were injected with CpG-DNA 1 mg/ml at a daily dose of 1 mg/kg for 4 days prior to sacrifice or were exposed to hypoxia alone. The severity of experimental NEC was graded using a previously validated scoring system from 0 (normal) to 3 (severe). At sacrifice, serum was obtained by retro-orbital puncture, and terminal ilea was harvested in 10% neutral buffered formalin or frozen in liquid nitrogen after embedding in Cryo-Gel (Cancer Diagnostics, Inc.). Where indicated, mucosal scrapings were obtained by microdissection under 20× power, and collected in RNAlater (Qiagen, Valencia, Calif.).

Immuno-analysis. Cells were grown and treated in 12-well plates on glass coverslips and fixed with 4% paraformaldehyde and permeabilized with 0.1% Triton X-100 (Sigma-Aldrich, St. Louis, Mo.), blocked 5% goat serum, and after immunostaining were imaged using an Olympus Fluoview 1000 confocal microscope under oil-immersion objectives. Images were cropped using Adobe Photoshop CS2 software (Adobe Systems Inc., San Jose, Calif.). In parallel, Cryo-Gel (Cancer Diagnostics, Inc.) frozen sections of terminal ileum were sectioned (4 μm), rehydrated with PBS and fixed with 2% paraformaldehyde. Non-specific binding was blocked with 5% bovine serum albumin (BSA). Sections were imaged on an Olympus Fluoview 1000 confocal microscope using oil immersion objectives.

Assessment of NFkB activation. IEC-6 enterocytes were treated with LPS (50 μg/ml, Sigma-Aldrich, St. Louis, Mo.) and/or CpG-DNA (1 μM) either alone or in combination for 1 hour and immunostained with antibodies against the p65 subunit of NF-κB. Quantification of nuclear translocation was performed as adapted from Ding, et al. J Biol. Chem. 1998 Oct. 30; 273(44):28897-905. A threshold limit was set based upon the emission signal for DRAQ5 staining, which defined a nuclear region of interest (ROI). Symetric expansion of the nuclear ROI by 12 pixels defined a nuclear and cytoplasmic ROI. The emission within this ROI was subjected to calculation of area, integrated intensity, and average intensity using MetaMorph software version 6.1 software. The average NF-κB p65 intensity of the cytoplasmic area was determined by subtracting the area and integrated intensity of the nuclear ROI from the nuclear+cytoplasmic ROI and dividing the cytoplasmic integrated intensity by the cytoplasmic area. The extent of p65 staining in the nucleus versus the cytoplasm (i.e. the nuclear to cytoplasmic ratio) was calculated for each cell by dividing the nuclear average NF-κB p65 intensity by the cytoplasmic average NF-κB p65 intensity. Nuclear to cytoplasmic ratio was calculated for more than 200 cells per treatment group for more than 4 separate experiments.

Statistical Analysis. Statistical analysis was performed using SPSS 13.0 software.s ANOVA was used for comparisons for experiments involving more that two experimental groups. Two-tailed student's t-test was used for comparison for experiments consisting of two experimental groups. For analysis of NEC severity, chi-square analysis was used.

Results

CpG-DNA was found to inhibit LPS-induced enterocyte apoptosis in murine models of endotoxemia as well as NEC. In a murine model of endotoxemia, immunohistochemical staining of terminal ileum of mice injected with either saline (FIG. 19A), LPS (FIG. 19B) or LPS and CpG-DNA (FIG. 19C) demonstrated that apoptosis occurring in the enterocytes of LPS-treated animals was substantially reduced in LPS and CpG-DNA treated animals. Similar findings were observed in mouse models of NEC (FIG. 19D-G, summarized in FIG. 19H). Administration of CpG-DNA to the NEC animals substantially reduced apoptosis.

FIG. 20A-I illustrates the anatomical and histologic correlates of the results presented in FIGS. 19D-G. Gross and histological micrographs of control and NEC mice treated with CpG-DNA demonstrate a substantial inhibition of the NEC pathology in CpG-DNA treated animals, as summarized in FIG. 20I.

Further, it was found that, when LPS-induced activation of NFκB (with subsequent translocation into the nucleus) was measured in IEC-6 cells, while CpG-DNA significantly inhibited translocation, the combination of CpG-DNA with the TLR4 antagonist polymixin B was even more effective at inhibiting translocation (FIG. 21). This indicates that the combination of a TLR9 agonist (e.g., CpG-DNA) with a TLR4 antagonist (polymixin B) has at least an additive effect in attenuating TLR4 signaling in enterocytes.

8. EXAMPLE 3

NOD2 expression in the intestine is reduced in human and experimental necrotizing enterocolitis. In order to define the molecular mechanisms that lead to the development of NEC, a newborn mouse model of this disease was developed that parallels the findings seen in human NEC (Leaphart et al., 2007, J. Immunology 179:4808-4820; Leaphart et al., 2007, Gastroenterology 132:2395-2411; Cetin et al., 2007, Am J Physiol Gastrointest Liver Physiol 292:G1347-1358). As is shown in FIG. 22A-I, newborn mice were randomized to be either breast-fed ("control", panels A, B) or gavaged with formula (Canine-Simialac 70%, water 30%) three times daily and subjected to 2 minutes of hypoxia (5% O2) in a Modular Incubator Hypoxic Chamber (Billups-Rothenberg) three times daily prior to each feeding ("NEC", panels C, D). Animals were killed on day 4 and the distal 2 cm of terminal ileum was harvested for histological and molecular analysis. The histological and gross appearance of the ileum in mice with experimental NEC (FIG. 22C, D) appears similar to that of the ileum in infants that undergo surgical resection for severe NEC (FIG. 22E, F), and serum levels of the pro-inflammatory cytokine interleukin-6 are increased in experimental NEC (panel G) similar to that observed in the clinical disease (Sharma et al., 2007, J Pediatr Surg 42:454-461).

Utilizing the experimental model described above, the importance of TLR4 signaling in the pathogenesis of NEC was defined. To do so, wild-type (C3H/HeOUJ) and TLR4-mutant mice (C3H/HeJ) mice were subjected to the model and the severity of NEC that developed was assessed by a blinded pathologist. As shown in FIG. 22H, the severity of NEC was significantly reduced in TLR4-mutant mice compared to wild-type littermates. Moreover, the expression of NOD2 was significantly reduced in mice with NEC compared to control mice, a similar finding to that observed in the intestine obtained from infants undergoing resection for severe NEC as compared to the expression in "control" infants at the time of stoma closure (FIG. 22I). Taken together, these findings indicate a critical role for TLR4 in the pathogenesis of NEC, and illustrate that the expression of NOD2 is reduced in NEC in mice and humans.

NOD2 activation with MDP inhibits TLR4 signaling in enterocytes. The next experiments were designed to determine whether NOD2 activation with MDP would inhibit TLR4 signaling in enterocytes. To do so, IEC-6 enterocytes—a cell line that represents a model system to study enterocyte biology and which expresses TLR4 (Neal et al., 2006, J Immunol 176:3070-3079)—were treated with LPS in the presence or absence of MDP. Since TLR4 signaling leads to the translocation of NFkB from the cytoplasm into the nucleus, the extent of TLR4 activation was evaluated using an immunofluorescence-based detection assay of the p65 subunit of NFkB. As is shown in FIG. 23A and quantified in FIG. 23E, in control cells, NFkB is localized in the cytoplasm. Upon treatment with LPS (50 μg, 1 h), NFkB was detected in the nucleus, indicative of NFkB activation (FIG. 23B). Importantly, treatment of cells with LPS in the presence of the NOD2 agonist MDP leads to a reduction in nuclear translocation and the persistence of NFkB in the cytoplasm (FIG. 23C). Treatment of IEC-6 cells with MDP alone did not significantly alter the extent of NFkB translocation (FIG. 23D).

The next series of experiments were designed to further define the physiological significance of the finding that MDP reduces TLR4-mediated NFkB translocation in enterocytes, and to evaluate potential mechanisms involved. Since NFkB activation is known to lead to the release of pro-inflammatory cytokines including IL-6, experiments were performed to evaluate whether MDP would alter the extent of IL-6 release from LPS-treated IEC-6 cells. As shown in FIG. 24A, treatment of IEC-6 cells in vitro with LPS led to a significant increase in IL-6 release compared with untreated cells, that was significantly reduced upon exposure to MDP. To determine the physiological significance of this work in vivo, wild-type and NOD2-knockout mice were injected with LPS (5 mg/kg) in the presence or absence of MDP (1 mg/kg), and serum IL-6 release—a measure of TLR4 signaling in vivo—was determined by ELISA. As is shown in FIG. 24B, MDP significantly reduced the extent of LPS-mediated IL-6 release in wild-type mice confirming a reduction in TLR4 signaling in vivo. The effects of MDP in reducing TLR4 signaling were less pronounced in NOD2-knockout mice, confirming the specificity of the effect of MDP for NOD2 (FIG. 24B).

To further define the effects of MDP on LPS-mediated signaling in enterocytes, IEC-6 cells were treated with LPS in the presence or absence of MDP and the expression of the TLR4 downstream target pERK was assessed by SDS-PAGE. As is shown in FIG. 24C, LPS caused an increase in the expression of pERK compared with untreated cells. Strikingly, pre-treatment with MDP significantly reduced the extent of pERK phosphorylation, and returned levels to that of untreated cells. Treatment of cells with the inactive isoform of MDP (i.e. MDPC) at equimolar concentrations in the presence of LPS did not reduce the extent of pERK expression (FIG. 24C) or IL-6 release. Taken together, these findings indicate that NOD2 activation with MDP leads to an inhibition of TLR4 signaling in enterocytes in vitro and in vivo.

MDP treatment of enterocytes reduces the expression of TLR4. The next series of studies investigated the potential mechanisms by which MDP activation of NOD2 could lead to a reduction in the extent of TLR4 signaling. It was first determined that MDP does not alter the relative distribution of TLR4 in enterocytes, as confirmed using immunohistochemistry. By contrast, MDP leads to a significant reduction in the expression of TLR4 in enterocytes (FIG. 25), suggesting a potential mechanism by which MDP could limit TLR4 signaling. Taken together, these findings suggest a potential mechanism by which MDP activation of NOD2 could inhibit TLR4 signaling.

MDP prevents against the development of experimental necrotizing enterocolitis. The previous experiments indicate that TLR4 plays a critical role in the pathogenesis of NEC, and that NOD2 activation with MDP inhibits TLR4 signaling in enterocytes. It was also determined that mucosal NOD2 expression is decreased in experimental NEC (FIG. 22I). These findings suggest that MDP administration may prevent the development of NEC. To test this directly, either saline (vehicle) or MDP (1 mg/ml, with each feed) were administered to NOD2-wild-type mice daily for four days, and then NEC was induced as in FIG. 22I. As shown in the histological sections obtained from the terminal ilea, saline treated mice developed severe NEC (FIG. 26C), while animals treated with MDP demonstrated a striking reduction in the extent of NEC that developed (FIG. 26D). Administration of MDP alone did not alter intestinal histology (FIG. 26B). These data support the hypothesis that NOD2 activation with MDP may represent a novel agent to protect against the development of experimental NEC.

Discussion. The foregoing experiments provide evidence that the NOD2 agonist MDP provides protection from the development of experimental NEC in newborn mice, a condition that has been shown to be dependent upon the activation of TLR4 (Leaphart et al., 2007, J. Immunology 179: 4808-4820). In terms of understanding the potential mechanism[s] involved, it has been found that MDP limits TLR4 signaling in enterocytes, potentially through an inhibition in TLR4 expression. The potential significance of these findings is found in the fact that MDP may be used to prevent NEC in infants who are at risk for its development. The ability to adopt potential preventive strategies is highlighted by the fact that infants at risk for NEC development represent a fairly well defined cohort—specifically premature infants that have been administered enteral formula. As such, an infant formula that contains agents that inhibit TLR4 signaling—such as MDP—may represent a novel and exciting therapeutic tool.

What are the potential mechanisms by which MDP may reduce the expression of TLR4 in enterocytes? It is possible that activation of downstream targets of NOD2 by MDP may lead to post-translational modification of TLR4 that could shorten its half-life. In support of this concept, Yang et al have shown that MDP may alter the ubiquitin state of the TLR4 target kinase Rip2, leading to a shortening of its half-life in macrophages (Yang et al., 2007, J Biol Chem 282:36223-36229); this suggests that MDP could alter the half-life of TLR4 by similarly altering the degree to which TLR4 is ubiquitinated. Alternatively, MDP could alter the efficiency or rate of transcription of TLR4, through mechanisms that remain to be defined. MDP may also limit TLR4 signaling through a variety of other mechanisms unrelated to the overall expression of TLR4, such as through effects on the interaction with the adapter protein MyD88, or other downstream targets including IRAK-1.

A link between mutations in NOD2 and inflammatory bowel disease has been suggested to implicate NOD2 signaling in the suppression of intestinal inflammation (Cho, 2007, Gastroenterology 133:1327-1339). Previous reports have demonstrated that the administration of MDP can limit the degree of intestinal inflammation in models of ulcerative colitis (Watanabe et al., 2008, J Clin Invest 118:545-559; Yang et al., 2007, Gastroenterology 133:1510-1521; Maeda et al., 2005, Science 307:734-738). Although previous reports show protection of MDP in models of ulcerative colitis, it is important to point out that ulcerative colitis and necrotizing enterocolitis are separate and unique diseases: ulcerative colitis affects adults and older children, NEC only affects preterm or term infants; ulcerative colitis presents with bloody diarrhea and abdominal pain, NEC presents with progressive and often overwhelming sepsis; ulcerative colitis is a chronic disease that is not fatal; NEC is an acute necrosis of the intestine that is fatal in nearly 50% of cases; the pathological hallmark of ulcerative colitis is that of intestinal inflammation confined to the mucosal lining of the intestine that never extends into the submucosa, the pathological hallmark of NEC is that of mucosal inflammation that always extends into the submucosa to extend to the full thickness of the intestine.

9. EXAMPLE 4

The effect of the TLR9 agonist CpG-ODN 5' TCGTCGTTTTGTCGTTCCTGACGTT 3' (SEQ ID NO:10; referred to herein as CpG-ODN-HS) on the mediator of activated TLR4, NFκB, was examined in a murine NEC model (previously described, above). The effect of CpG-ODN-HS on inflammation in the NEC murine model was also examined as a measured by TNF-α expression, which is an index of inflammation.

Materials and methods. Phosphorothioated CpG-ODN-HS and oligodeoxynucleotide (ODN) 1826 (TCCATGACGT-TCCTGACGTT) (SEQ ID NO:6; referred to herein as CpG-DNA) were synthesized by the University of Pittsburgh DNA synthesis facility. ODNs were confirmed to be endotoxin-free by Limulus assay. NFkB-GFP antibody was obtained from Santa Cruz and Abcam. The extent of nuclear translocation was determined in an adaptation of the methodology of Ding and colleagues. In brief, a threshold limit was set based upon the emission signal for the nuclear stain DRAQ5, which therefore defined a nuclear region of interest (ROI). To define a corresponding cytoplasmic region of interest, a circular region 12 pixels beyond the nucleus was stenciled upon each cell. The average integrated pixel intensity pertaining to the corresponding NFkB emission within the cytoplasmic and nuclear regions was then determined for more than 200 cells per treatment group in at least four experiments per group, using MetaMorph software version 6.1 (Molecular Devices Corporation, Downingtown, Pa.).

Mucosal TNF-α expression was measured using quantitative real-time PCR (RTPCR). Quantitative real-time PCR in cultured enterocytes and intestinal tissue using the BioRad iCycler (Biorad, Hercules, CA) was performed as in (Leaphart, C. L., J. Cavallo, S. C. Gribar, S. Cetin, J. Li, M. F. Branca, T. D. Dubowski, C. P. Sodhi, and D. J. Hackam. 2007. A Critical Role for TLR4 in the Pathogenesis of Necrotizing Enterocolitis by Modulating Intestinal Injury and Repair. *J Immunology* 179:4808-4820). Oligonucleotide primer pairs used for RTPCR were as follows: forward: 5' CATCTTCT-CAAAATTCGAGTGACAA 3' (SEQ ID NO:14), reverse: 5' CCCAACATGGAACAGATGAGGGT 3' (SEQ ID NO:15); and forward: 5' TTCCGAATTCACTGGAGCCTCGAA 3' (SEQ ID NO:16), reverse: 5' AAGGTCTAAGAAGG-GACTCCACGT 3' (SEQ ID NO:17). Gene expression was normalized to β-actin expression. Where indicated, gene expression was assessed on 2.5% agarose gels using ethidium bromide staining. Images were obtained with a Kodak (New Haven, CT) Gel Logic 100 Imaging System using Kodak (New Haven, CT) Molecular Imaging software.

Induction of necrotizing enterocolitis. Transgenic mice expressing NFkB-GFP were used for both control and experimental groups. To induce experimental NEC, 10-14 day-old mice were gavage fed (Similac Advanced infant formula (Ross Pediatrics): Esbilac canine milk replacer at a ratio of 2:1) five times daily, and exposed to intermittent hypoxia (5% $O_2$, 95% $N_2$) for 10 minutes using a modular hypoxic chamber (Billups-Rothenberg, DelMar, Calif.) twice daily for 4 days. Animals were fed 200 microliters per 5 grams of mouse body weight by gavage over 2-3 minutes, using a 24-French angio-catheter which was placed into the mouse esophagus under direct vision. Samples were harvested at day four for analysis. It has been demonstrated that this experimental protocol induces intestinal inflammation and the release of pro-inflammatory cytokines in a pattern that closely resembles human NEC. Control (i.e., non NEC) animals remained with their mothers and received breast milk. Where indicated, NEC or breast fed animals of all strains were injected with CpG-DNA 1 mg/ml at a daily dose of 1 mg/kg for 4 days prior to. The severity of experimental NEC was graded using a previously validated scoring system from 0 (normal) to 4 (severe). At sacrifice, serum was obtained by retro-orbital puncture, and terminal ilea was harvested in 10% neutral buffered formalin or frozen in liquid nitrogen after embedding in Cryo-Gel (Cancer Diagnostics, Inc.). Mucosal scrapings were obtained by microdissection under 20× power, and collected in RNAlater (Qiagen, Valencia, Calif.) for RTPCR analysis. Histological (H&E) analysis if terminal ileum was also performed.

Immuno-analysis. Cryo-Gel (Cancer Diagnostics, Inc.) frozen sections of terminal ileum were sectioned (4 μm), rehydrated with PBS and fixed with 2% paraformaldehyde. Non-specific binding was blocked with 5% bovine serum albumin (BSA). Sections were imaged on an Olympus Fluoview 1000 confocal microscope using oil immersion objectives. The ileum sections were immunostained with antibodies against the green fluorescent protein of the NFκB-GFP.

Results

Figure 27:
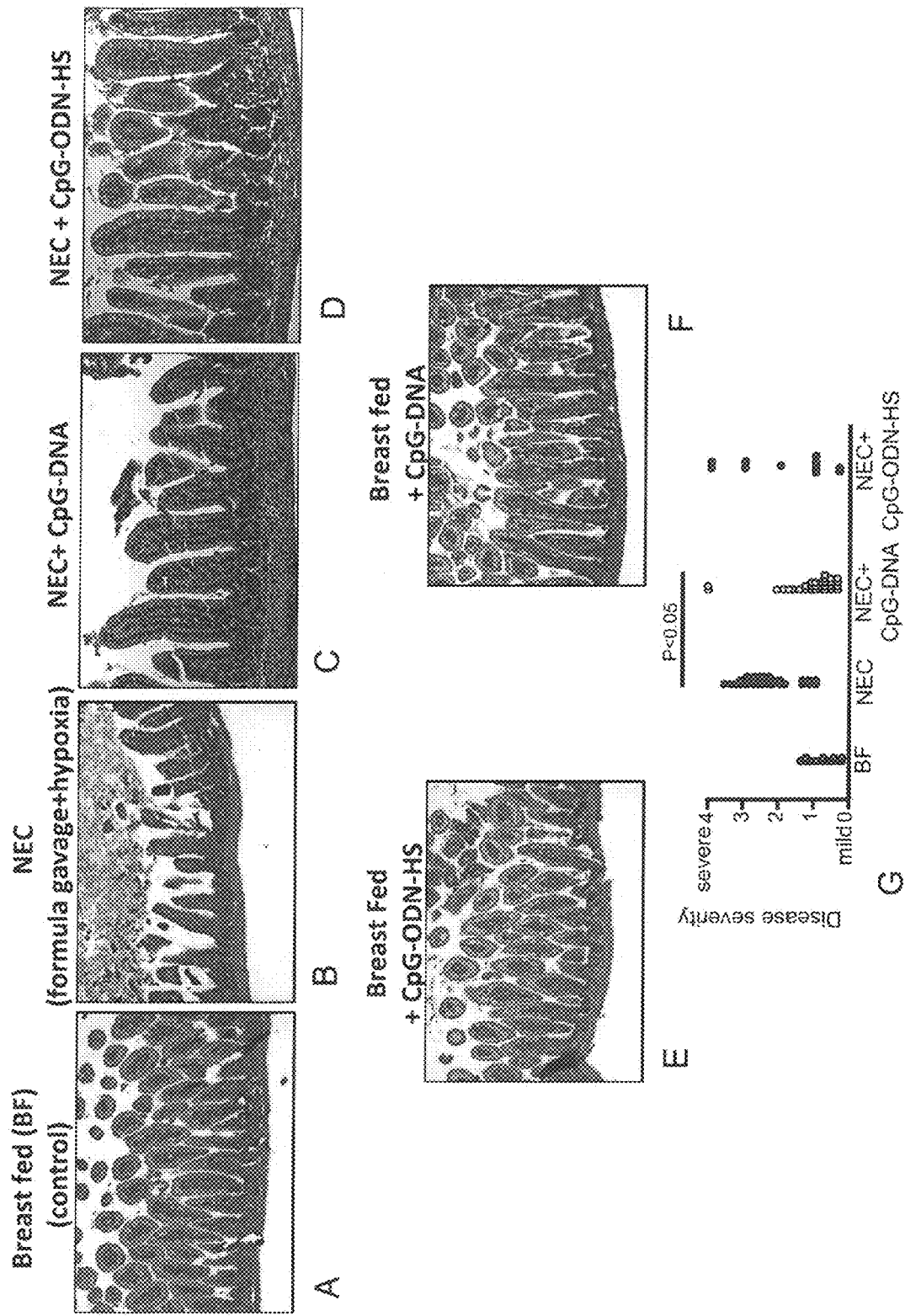

NEC mice exhibited more severe mucosal injury in terminal ileum than breast-fed mice (FIGS. 27A, B and G). Histological micrographs of control and NEC mice treated with CpG-ODN-HS and CpG-DNA demonstrate an inhibition of the NEC pathology in treated animals (FIGS. 27C, D and G). Additionally, mucosal TNF-α expression in the terminal ileum was increased in the NEC mice compared to the breast fed control mice, indicating an increase in inflammatory response in the NEC mice. Treating the NEC mice with CpG-ODN-HS or CpG-DNA reduced the level of expression of mucosal TNF-α (FIG. 28). Further, activation of NFκB in NEC cells was increased compared to the breast fed controls, but was reduced when the NEC mice were treated with CpG-ODN-HS (FIG. 29A-D). FIGS. 30A-C show the colocalization of NFκB (i.e., NFκB-GFP) and E-cadherin in ilea cells of control mice (A), NEC mice (B) and NEC mice treated with CpG-ODN-HS.

Various publications are cited herein, the contents of which are hereby incorporated by reference in their entireties.

What is claimed:

1. A method of treating necrotizing enterocolitis in a subject in need of such treatment comprising administering, to the subject, an effective amount of a TLR9 agonist oligonucleotide comprising one or more copy of 5' GTCGTT 3' (SEQ ID NO:11).

2. The method of claim 1, where the oligonucleotide further comprises 5' GACGTT 3' (SEQ ID NO:18).

3. The method of claim 2, where the oligonucleotide comprises 5' TCGTCGTTTTGTCGTTCCTGACGTT 3' (SEQ ID NO:10).

4. The method of claim 1, where the oligonucleotide is orally administered.

* * * * *

UNITED STATES PATENT AND TRADEMARK OFFICE
CERTIFICATE OF CORRECTION

| | | |
|---|---|---|
| PATENT NO. | : 8,518,903 B2 | Page 1 of 1 |
| APPLICATION NO. | : 13/068553 | |
| DATED | : August 27, 2013 | |
| INVENTOR(S) | : David J. Hackam | |

It is certified that error appears in the above-identified patent and that said Letters Patent is hereby corrected as shown below:

IN THE SPECIFICATION:

At column 1, line 17:

"The TLR4 and TLR9-related subject matter of this application was made with government support under Grant No. R01-GM078238-01 awarded by the National Institutes of Health. The United States Government has certain rights in the invention. No federal funds were used in the development of subject matter related to NOD2."

should read

-- This invention was made with government support under grant numbers R01-GM078238-01 and DK083752 awarded by the National Institutes of Health. The government has certain rights in the invention. --

Signed and Sealed this
Twenty-first Day of October, 2014

Michelle K. Lee
*Deputy Director of the United States Patent and Trademark Office*

SEQUENCE LISTING

<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 1
tcgtcgtttt gtcgttttgt cgtt                                          24

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
gggggacgat cgtcgggggg                                               20

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 3
tcgtcgtcgt tcgaacgacg ttgat                                         25

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 4
tcgtcgtttt gtcgttttgt cgtt                                          24

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (11)..(12)

<223> OTHER INFORMATION: glycerol linker between nucleotides 11 and 12

<400> SEQUENCE: 5
tctgtcgttc ttcttgctgt ct                                          22

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
tccatgacgt tcctgacgtt                                             20

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: N3-Me-dC
<220> FEATURE:
<221> NAME/KEY: misc_feature
<222> LOCATION: (11)..(12)
<223> OTHER INFORMATION: glycerol linker between nucleotides 11 and 12
<220> FEATURE:
<221> NAME/KEY: misc_feature
<222> LOCATION: (18)..(18)
<223> OTHER INFORMATION: N3-Me-dC

<400> SEQUENCE: 7
tctgtcgttc ttcttgctgt ct                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: N1-Me-dG
<220> FEATURE:
<221> NAME/KEY: misc_feature
<222> LOCATION: (11)..(12)
<223> OTHER INFORMATION: glycerol linker between nucleotides 11 and 12
<220> FEATURE:
<221> NAME/KEY: misc_feature
<222> LOCATION: (17)..(17)
<223> OTHER INFORMATION: N1-Me-dG

<400> SEQUENCE: 8
tctgtcgttc ttcttgctgt ct                                          22

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tccatgagct tcctgagctt                                             20

<210> SEQ ID NO 10

```
<211> LENGTH: 25
<212> TYPE: DNA
<213> ORGANISM: Artificial Sequence
<220> FEATURE:
<223> OTHER INFORMATION: Synthetic Organism

<400> SEQUENCE: 10
tcgtcgtttt gtcgttcctg acgtt                                          25

<210> SEQ ID NO 11
<211> LENGTH: 11
<212> TYPE: DNA
<213> ORGANISM: Artificial Sequence
<220> FEATURE:
<223> OTHER INFORMATION: Synthetic Organism

<400> SEQUENCE: 11
gtcgttttgt c                                                         11

<210> SEQ ID NO 12
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 12
tcgtcgtttt gtc                                                       13

<210> SEQ ID NO 13
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 13
tcctgacgtt                                                           10

<210> SEQ ID NO 14
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 14
catcttctca aaattcgagt gacaa                                          25

<210> SEQ ID NO 15
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 15
cccaacatgg aacagatgag ggt                                            23

<210> SEQ ID NO 16
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 16
```

```
ttccgaattc actggagcct cgaa                                          24

<210> SEQ ID NO 17
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 17
aaggtctaag aagggactcc acgt                                          24
```